United States Patent
Komazaki et al.

(10) Patent No.: US 11,005,232 B2
(45) Date of Patent: May 11, 2021

(54) LIGHT SOURCE DEVICE

(71) Applicant: OLYMPUS CORPORATION, Tokyo (JP)

(72) Inventors: Iwao Komazaki, Saitama (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/212,770

(22) Filed: Dec. 7, 2018

(65) Prior Publication Data

US 2019/0109435 A1 Apr. 11, 2019

Related U.S. Application Data

(63) Continuation of application No. PCT/JP2016/067097, filed on Jun. 8, 2016.

(51) Int. Cl.
*H01S 3/00* (2006.01)
*H01S 5/0683* (2006.01)
(Continued)

(52) U.S. Cl.
CPC ...... *H01S 5/06835* (2013.01); *A61B 1/00029* (2013.01); *A61B 1/00032* (2013.01); *A61B 1/00036* (2013.01); *A61B 1/063* (2013.01); *A61B 1/0669* (2013.01); *H01S 5/0428* (2013.01); *H01S 5/0617* (2013.01); *H01S 5/0651* (2013.01); *H01S 5/06253* (2013.01); *H01S 5/005* (2013.01); *H01S 5/06804* (2013.01)

(58) Field of Classification Search
CPC ..... H01S 5/068–06837; H01S 5/06825; H01S 5/06835; H01S 5/06216; H01S 5/0427–0428
See application file for complete search history.

(56) References Cited

U.S. PATENT DOCUMENTS 6,091,747 A * 7/2000 Morita ............ H01S 5/042
372/26
6,563,848 B1 5/2003 Iwazaki
(Continued)

FOREIGN PATENT DOCUMENTS

| JP | H10-261827 A | 9/1998 |
|---|---|---|
| JP | 2001-053377 A | 2/2001 |

(Continued)

OTHER PUBLICATIONS

Japanese Office Action dated Nov. 12, 2019 in Japanese Patent Application No. 2018-522233.
(Continued)

*Primary Examiner* — Tod T Van Roy
*Assistant Examiner* — Delma R Fordé
(74) *Attorney, Agent, or Firm* — Scully, Scott, Murphy & Presser, P.C.

(57) ABSTRACT

A light source device includes a laser diode configured to emit a laser light used as an illumination light, a determination unit configured to determine one of a plurality of modes as an operation mode of the laser diode based on usage state of the light source device; and a driver configured to drive the laser diode in a condition that a bias current to the laser diode is applied depending on the operation mode determined by the determination unit.

5 Claims, 16 Drawing Sheets

(51) Int. Cl.
*A61B 1/00* (2006.01)
*H01S 5/0625* (2006.01)
*A61B 1/06* (2006.01)
*H01S 5/042* (2006.01)
*H01S 5/06* (2006.01)
*H01S 5/065* (2006.01)
*H01S 5/00* (2006.01)
*H01S 5/068* (2006.01)

(56) References Cited

U.S. PATENT DOCUMENTS

| | | | |
|---|---|---|---|
| 2005/0259091 A1* | 11/2005 | Sakamoto | H01S 5/06832 345/204 |
| 2006/0159140 A1* | 7/2006 | Machida | H01S 3/0602 372/33 |
| 2009/0062617 A1 | 3/2009 | Mizuyoshi | |
| 2009/0214198 A1* | 8/2009 | Takahashi | H01S 5/06825 398/1 |
| 2011/0228037 A1* | 9/2011 | Omori | G03G 15/04072 347/247 |
| 2014/0314112 A1 | 10/2014 | Budai | |
| 2016/0315713 A1* | 10/2016 | Chow | H04B 10/504 |
| 2016/0367124 A1* | 12/2016 | Nishio | H01S 5/06804 |

FOREIGN PATENT DOCUMENTS

| | | |
|---|---|---|
| JP | 2001-257416 A | 9/2001 |
| JP | 2001-258837 A | 9/2001 |
| JP | 2009-056248 A | 3/2009 |

OTHER PUBLICATIONS

International Search Report dated Aug. 16, 2016 issued in PCT/JP2016/067097.
English translation of International Preliminary Report on Patentability dated Dec. 20, 2018 together with the Written Opinion received in related International Application No. PCT/JP2016/067097.
Chinese Office Action dated Oct. 23, 2020 in Chinese Patent Application No. 201680086529.7.

* cited by examiner

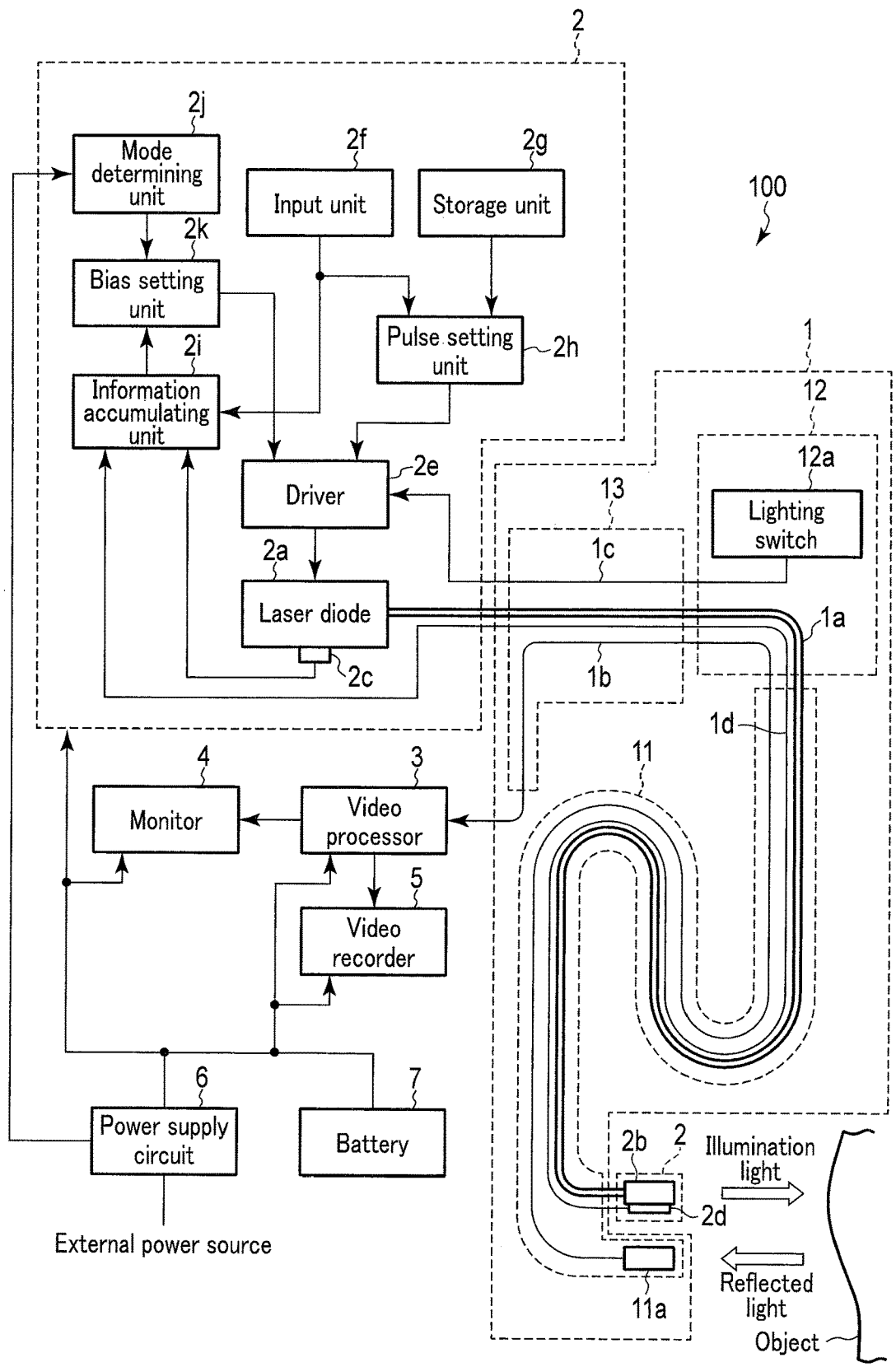
F I G. 1

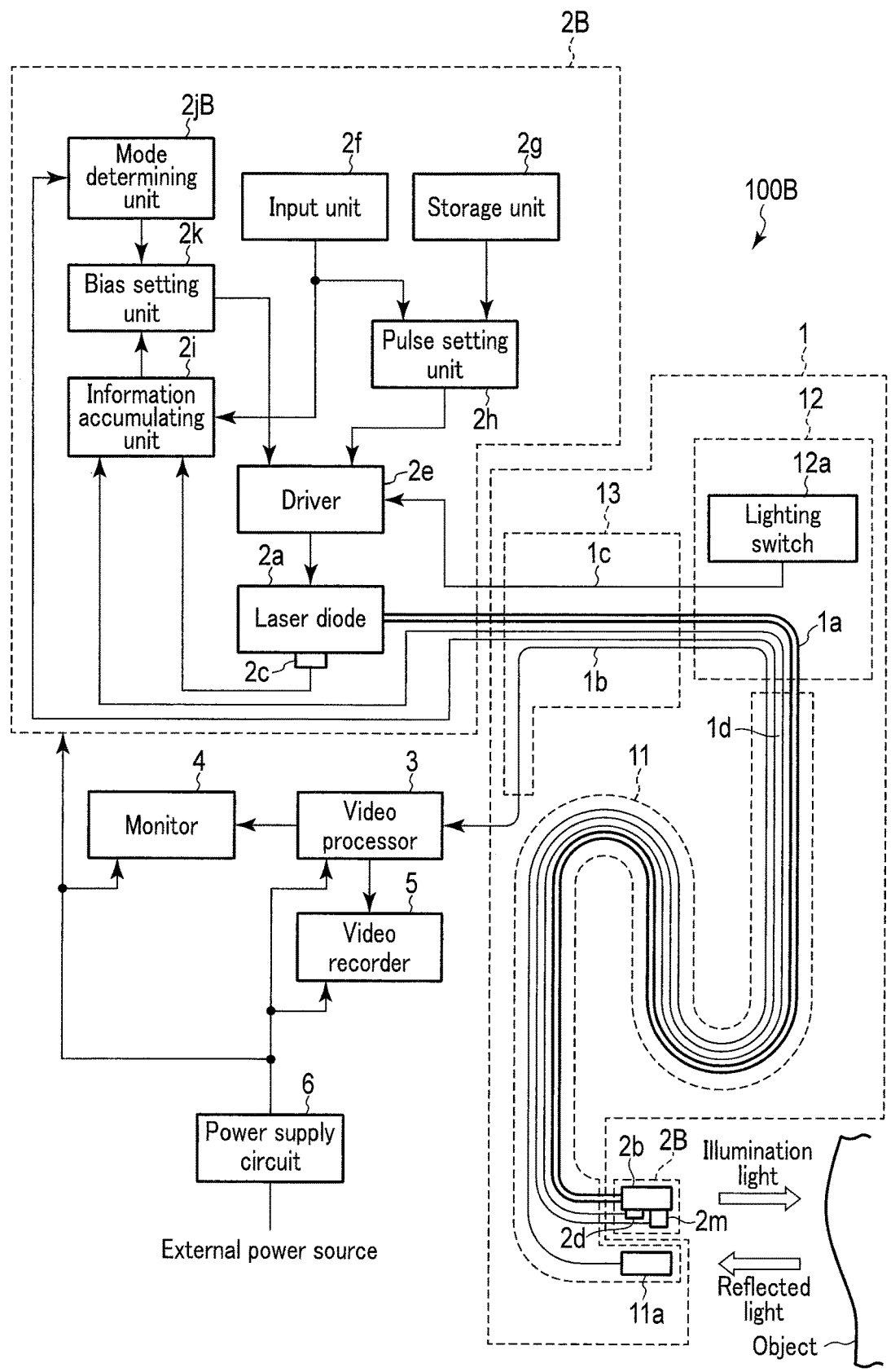
F I G. 5

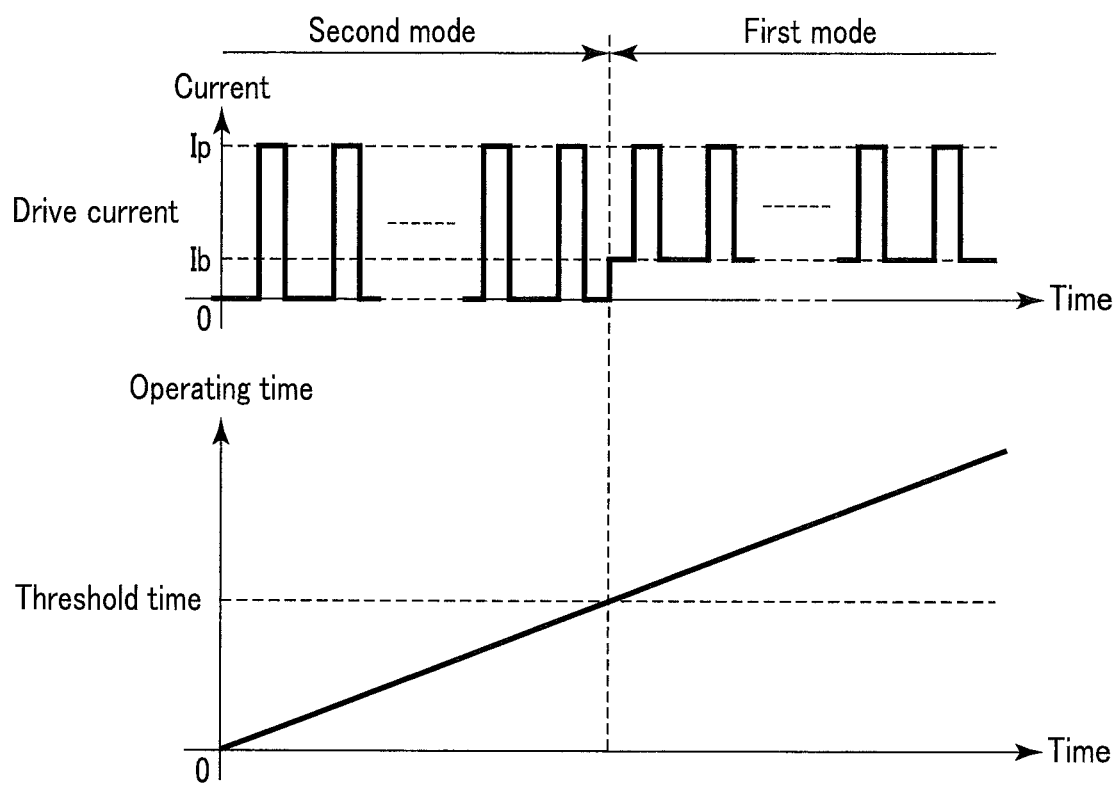
F I G. 6

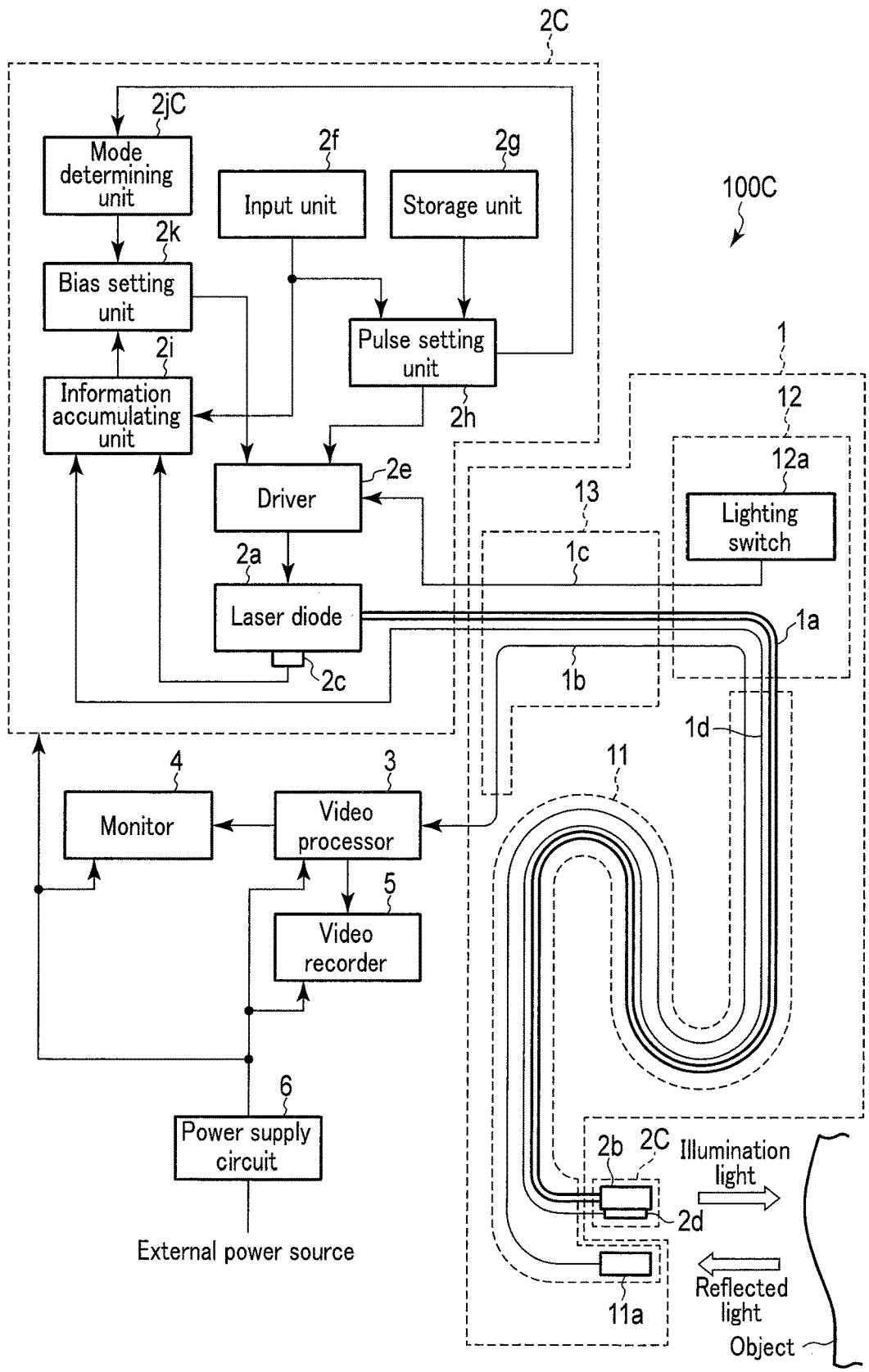
F I G. 7

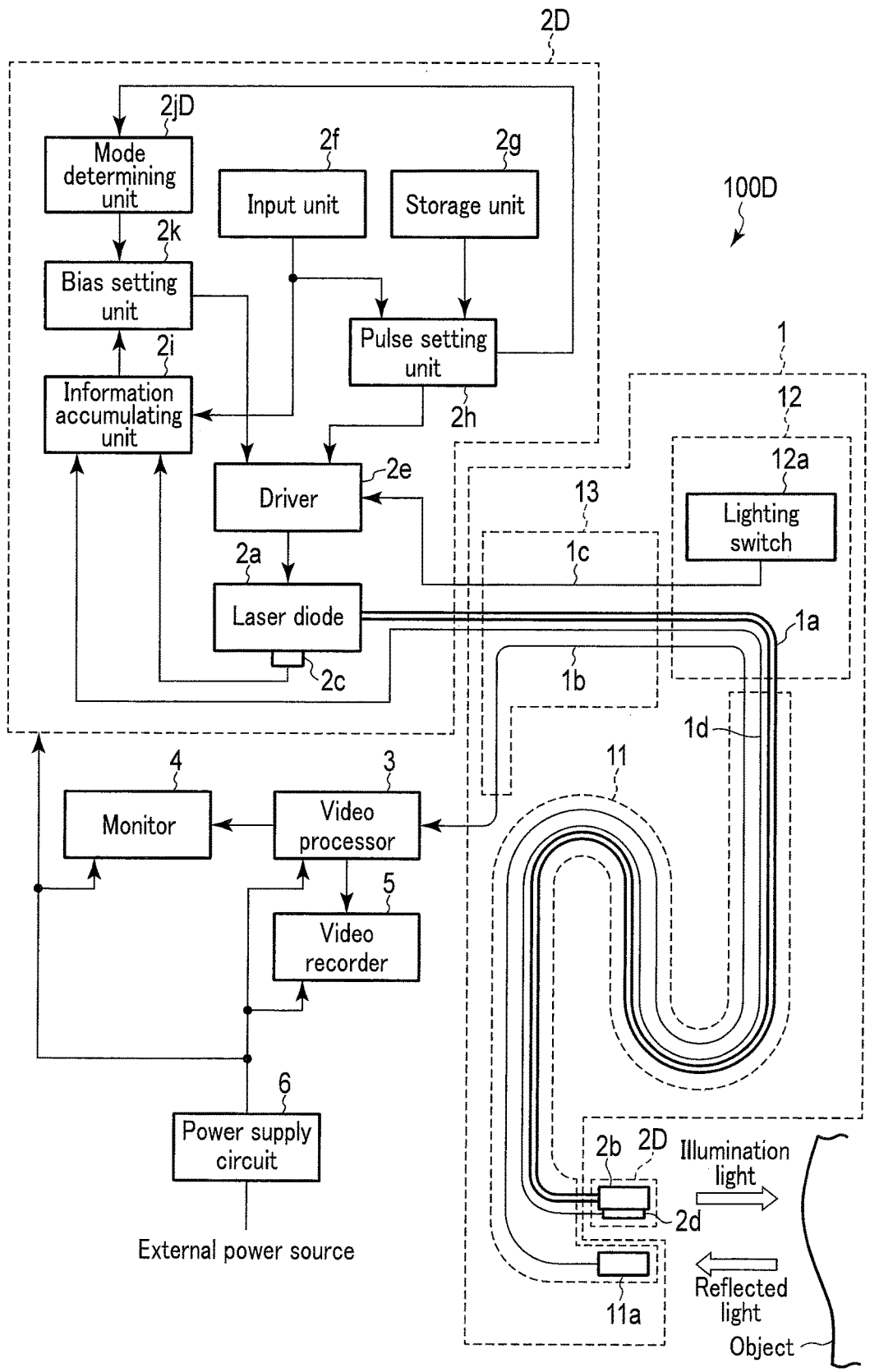
F I G. 10

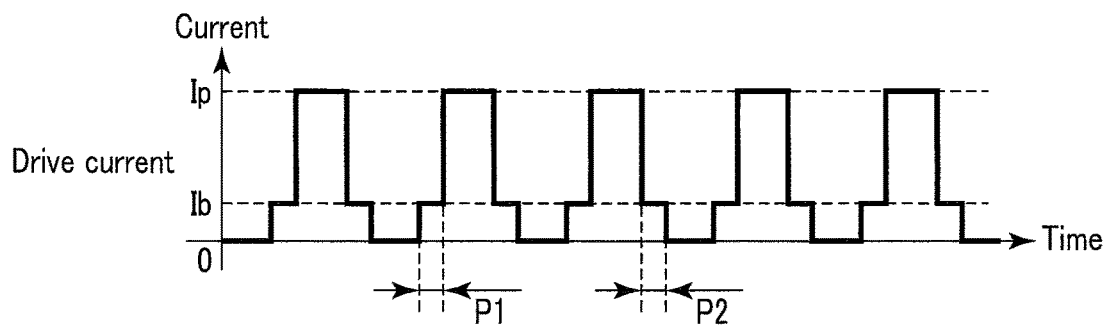
F I G. 18
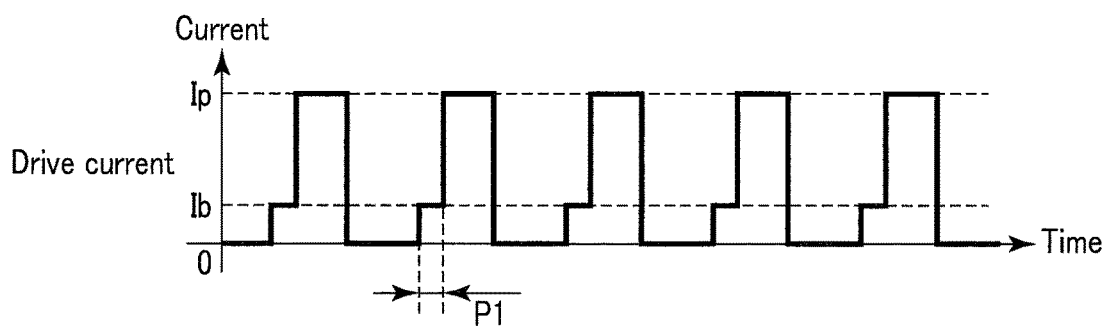
F I G. 19
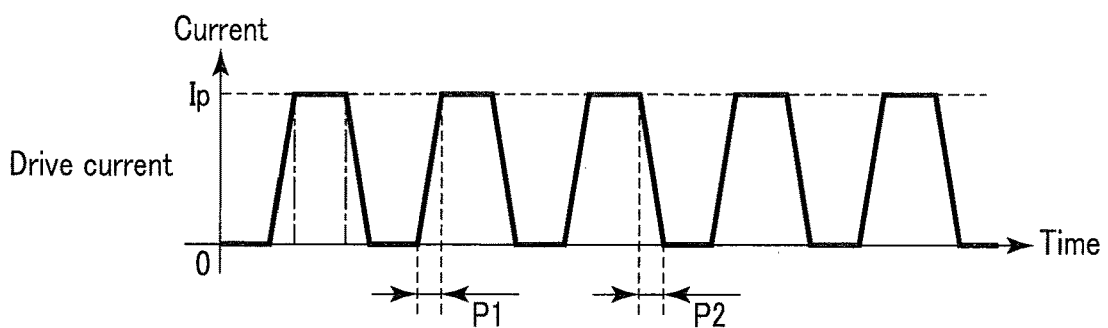
F I G. 20

LIGHT SOURCE DEVICE

CROSS-REFERENCE TO RELATED APPLICATIONS

This application is a Continuation Application of PCT Application No. PCT/JP2016/067097, filed Jun. 8, 2016, the entire contents of all of which are incorporated herein by reference.

BACKGROUND OF THE INVENTION

1. Field of the Invention

The present invention relates to a light source device.

2. Description of the Related Art

An endoscope system includes a light source device that emits a light for illuminating an object using a laser diode. In this type of light source device, the brightness of the illumination light can be adjusted by changing the amount of the light emission of the laser diode.

For example, Jpn. Pat. Appln. KOKAI Publication 2009-56248 discloses a technique in which a discrete drive current is applied to a light source in a fixed period, and the number, the magnitude, or the time of application of the drive current in the fixed period is increased or decreased.

According to the technique disclosed in Jpn. Pat. Appln. KOKAI Publication 2009-56248, a laser diode changes in a very short time from a state in which no drive current is applied at all to a high-output laser mode, after going through an LED emission mode and a laser oscillation mode. Thereafter, the laser diode changes in a very short time in an order opposite to that described above to a state in which no drive current is applied at all. Such state changes are repeated at a high frequency.

BRIEF SUMMARY OF THE INVENTION

According to an aspect of the invention, light source device of the present invention includes: a laser diode configured to emit a laser light used as an illumination light; a determination unit configured to determine one of a plurality of modes as an operation mode of the laser diode; and a driver configured to drive the laser diode in a condition that a bias current to the laser diode is applied depending on the operation mode determined by the determination unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a configuration of an endoscope system according to the first embodiment.

FIG. 5 is a block diagram showing a configuration of an endoscope system according to a third embodiment.

FIG. 6 is a diagram showing a relationship between an operating time and a state of a drive current.

FIG. 7 is a block diagram showing a configuration of an endoscope system according to a fourth embodiment.

FIG. 10 is a block diagram showing a configuration of an endoscope system according to a fifth embodiment.

FIG. 18 is a diagram showing a first modification of the application state of a drive current in a first mode.

FIG. 19 is a diagram showing a second modification of the application state of a drive current in the first mode.

FIG. 20 is a diagram showing a third modification of the application state of a drive current in the first mode.

DETAILED DESCRIPTION OF THE INVENTION

Figure 2:
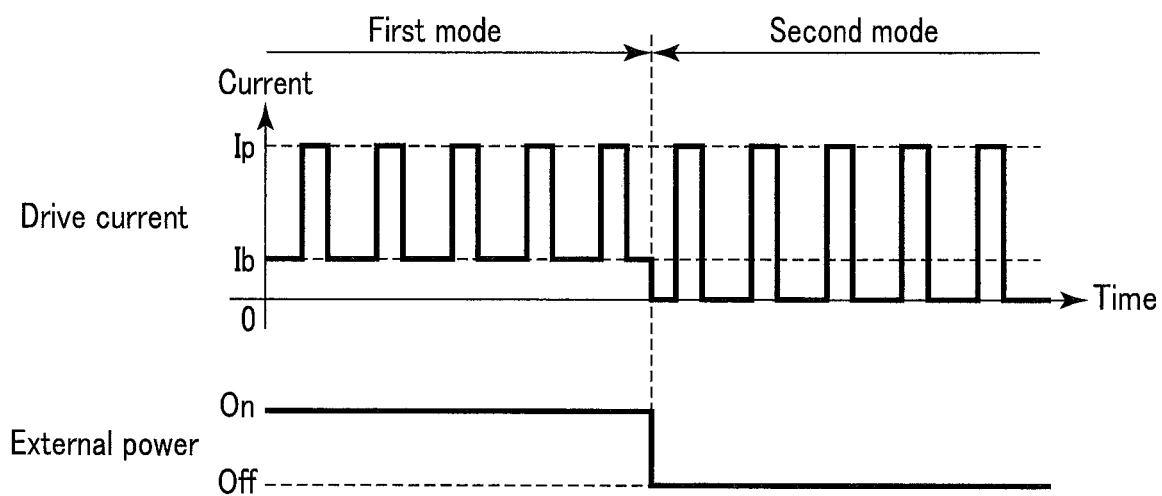
FIG. 2 is a diagram showing a relationship between a supply state of an external power source and a state of a drive current.

Hereinafter, some embodiments of the present invention will be described in detail with reference to the accompanying drawings.

First Embodiment

FIG. 1 is a block diagram showing a configuration of an endoscope system 100 according to the first embodiment. The endoscope system 100 includes an endoscope 1, a light source device 2, a video processor 3, a monitor 4, a video recorder 5, a power supply circuit 6, and a battery 7.

The endoscope 1 captures an image of the inside of a duct such as a lumen of a patient or the like. In the present embodiment, the endoscope 1 will be described as being for medical use, but the endoscope 1 need not be limited thereto. Namely, the endoscope 1 may be for industrial use in which to capture an image of the inside of a pipe line of an industrial product such as a pipe. Also, the endoscope 1 may be a front-viewing endoscope or a side-viewing endoscope.

The endoscope 1 includes an insertion module 11, an operation module 12, and a universal cord 13. A proximal end of the insertion module 11 is connected to the operation module 12. A distal end of the universal cord 13 is connected to the operation module 12. A proximal end of the universal cord 13 is branched, and connectors (not shown) are respectively arranged at the branches of the proximal end, so that the universal cord 13 can be detachably connected to the light source device 2 and the video processor 3.

The endoscope 1 also includes a light guide 1a and signal cables 1b, 1c, and 1d. The endoscope 1 may be provided with a tube (not shown) for air supply and water supply, as well known. The light guide 1a and the signal cable 1c leads from a distal end of the insertion module 11 to the light source device 2 via the insertion module 11, the operation module 12, and the universal cord 13. The signal cable 1b leads from the distal end of the insertion module 11 to the video processor 3 via the insertion module 11, the operation module 12, and the universal cord 13. The signal cable 1d leads from the operation module 12 to the light source device 2 via the universal cord 13.

The insertion module 11 has a thickness that allows the insertion module 11 to be inserted into a duct to be imaged, is long and narrow, and is flexible enough to be freely bendable. A light converting member 2b, a light amount sensor 2d, and a video camera 11a are arranged at the distal end of the insertion module 11. In this manner, the light converting member 2b and the light amount sensor 2d are physically stored in the insertion module 11, but functionally belong to the light source device 2. The light converting member 2b is connected to a distal end of the light guide 1a. The light converting member 2b converts some of the optical characteristics of a laser light propagated through the light guide 1a, to thereby generate an illumination light and emit it toward an object. The light converting member 2b will be detailed later. The video camera 11a incorporates an object lens and an image sensor, and converts an image formed by a reflected light from an object, that is, an image of an object into an electric signal (video signal). The video camera 11a sends the video signal to the signal cable 1b.

The operation module 12 is gripped by an operator of the endoscope 1. Although not shown, the operation module 12 includes an angle knob or the like for changing a direction of the distal end of the insertion module 11, as well known. The operation module 12 also includes a lighting switch 12a. The lighting switch 12a is operated by an operator to turn on/off an illumination light. The operation state of the lighting switch 12a is detected by the light source device 2 via the signal cable 1b leading to the light source device 2 via the universal cord 13.

A wire and a treatment instrument channel (not shown) leading from the operation module 12 to the distal end of the insertion module 11 may be provided in the insertion module 11 and the operation module 12, as well known. The wire changes the direction of the distal end of the insertion module 11 in accordance with the operation of the angle knob. The treatment instrument channel is open to the outside at the distal end of each of the operation module 12 and the insertion module 11. The treatment instrument channel guides, to the distal end side of the insertion module 11, a treatment instrument inserted from the operation module 12 side.

The light source device 2 includes a laser diode 2a, the light converting member 2b, a temperature sensor 2c, the light amount sensor 2d, a driver 2e, an input unit 2f, a storage unit 2g, a pulse setting unit 2h, an information accumulating unit 2i, a mode determining unit 2j, and a bias setting unit 2k.

The laser diode 2a emits a laser light in response to a drive current supplied from the driver 2e. For example, a multi-mode high-output blue laser light emitting element of a maximum power W class can be used as the laser diode 2a. However, the laser diode 2a is not limited to a device that emits a blue light having a wavelength of around 450 nm, and may emit a blue-violet light having a wavelength of around 405 nm, a green light having a wavelength of around 530 nm, a red light having a wavelength of around 640 nm, or the like. Furthermore, the laser diode 2a may emit a light with a plurality of different wavelengths while maintaining the light amount ratio among them. In the present embodiment, only one laser diode 2a is provided. However, a plurality of laser diodes 2a may be provided.

The light converting member 2b is, for example, a yttrium aluminum garnet (YAG) phosphor. The light converting member 2b converts the optical characteristics of a laser light, which is a primary light guided by the light guide 1a, and emits an illumination light as a secondary light. The light converting member 2b may be, for example, a diffusing member that widens a divergence angle of the primary light and emits it as a safe secondary light.

The temperature sensor 2c detects a temperature of the laser diode 2a.

The light amount sensor 2d detects an amount of the laser light emitted from the light converting member 2b. The amount of light detected by the light amount sensor 2d is transmitted to the information accumulating unit 2i of the light source device 2 by the signal cable 1d that passes through the insertion module 11, the operation module 12, and the universal cord 13.

The driver 2e applies, to the laser diode 2a, a drive current for causing the laser diode 2a to emit light according to the pulse conditions and the bias conditions set by the pulse setting unit 2h and the bias setting unit 2k. The driver 2e outputs a pulse current as the drive current. The driver 2e is an example of a driver configured to drive the laser diode 2a in a condition that a bias current to the laser diode is applied depending on an operation mode determined as described later.

The input unit 2f inputs a set value of an amount of light of the laser diode 2a accumulated in a predetermined period, in accordance with an operation by an operator.

The storage unit 2g stores a first table showing the characteristics (I-L characteristics) of the light output of the laser diode 2a with respect to the applied current and a second table showing the characteristics of the power conversion efficiency WP with respect to the applied current. The first and second tables show, as an example, each characteristic in a temperature range of ambient temperature 25° C. to 70° C. Specifically, for each of a plurality of accumulated light amounts, the first table (set data) shows the pulse conditions of the drive current to be applied to the laser diode 2a under the environment where the ambient temperature is the standard temperature (predetermined temperature), so that an amount of an illumination light accumulated within a predetermined period comes close to the respective accumulated light amounts. The pulse conditions of the drive current are defined by a pulse width (pulse time width) Tw, the number N of pulses, and a pulse amplitude Id. The standard temperature is discretionary, but is, for example, 25° C. Also, for each of a plurality of ambient temperatures at predetermined temperature intervals excluding the standard temperature within the aforementioned temperature range, the first table shows correction information for correcting a drive current for obtaining, under the environment of the ambient temperatures, an illumination light similar to that obtained under the environment of the standard temperature. The correction information is an amount of change of at least one of the pulse amplitude Id or a duty ratio. When a plurality of laser diodes 2a are provided in the light source device 2, the storage unit 2g stores the first and second tables related to the plurality of laser diodes 2a, and also stores information on the light amount ratio between the plurality of laser diodes 2a.

Based on the information stored in the storage unit 2g, the pulse setting unit 2h sets the conditions of a pulse current for setting the amount of light of the laser diode 2a accumulated in a predetermined period to the set value input by the input unit 2f. The pulse setting unit 2h notifies the driver 2e of the conditions as the pulse conditions.

The information accumulating unit 2i accumulates information on the usage state of the light source device 2 and the stability characteristics of the laser diode 2a. The information on the stability characteristics includes, for example, the following information: (1) a frequency of setting the aforementioned set value input by the input unit 2f; (2) an amount of light detected by the light amount sensor 2d; (3) the characteristics of an ambient temperature Ta of the laser diode 2a; (4) a temperature detected by the temperature sensor 2c; and (5) the characteristics of the conversion efficiency WP of the optical power with respect to the pulse amplitude Id of the drive current.

The mode determining unit 2j determines one of a first mode or a second mode as an operation mode of the light source device 2. The first mode is a mode for keeping the reliability of the laser diode 2a high. The second mode is a mode in which the aforementioned reliability is lower than in the first mode, but which can reduce the power consumption as compared to the first mode. The mode determining unit 2j determines an operation mode based on an operation state of the power supply circuit 6.

The bias setting unit 2k sets a magnitude of a bias current based on the information accumulated in the information accumulating unit 2i and the operation mode determined by the mode determining unit 2j. Then, the bias setting unit 2k notifies the driver 2e of the magnitude of the bias current as a bias condition.

The video processor 3 processes a video signal sent from the video camera 11a via the signal cable 1b, and generates a moving image to be displayed on the monitor 4.

The monitor 4 displays the moving image generated by the video processor 3. Various well-known display devices can be suitably used as the monitor 4. For example, a color liquid crystal display device is used as the monitor 4.

The video recorder 5 records the moving image generated by the video processor 3.

The power supply circuit 6 obtains electric power for operating the light source device 2, the video processor 3, the monitor 4, and the video recorder 5 from an external power source such as a commercial power source, and supplies the power to each component.

When the power supply circuit 6 is supplying power to each component, the battery 7 is charged by the power. When the power supply circuit 6 does not supply power to each component, the battery 7 supplies stored power to the light source device 2, the video processor 3, the monitor 4, and the video recorder 5.

Next, an operation of the endoscope system 100 configured as described above will be described.

(Basic Operation)

When an operator operates the lighting switch 12a in a state where no illumination light is emitted from the distal end of the insertion module 11, this fact is conveyed to the driver 2e via the signal cable 1d. In response to this, the driver 2e starts applying a drive current to the laser diode 2a.

The laser diode 2a operates by the drive current and emits a laser light. The laser light is propagated to the light converting member 2b while being guided by the light guide 1a. Then, the optical characteristics of the laser light are converted by the light converting member 2b, and emitted to the outside of the insertion module 11 as an illumination light. If an object faces the distal end of the insertion module 11, as shown in FIG. 1, the object is illuminated by the illumination light. Thus, the endoscope 1 functions as an illumination unit that emits a light emitted by the light source device 2 as an illumination light for illuminating the object.

An image of an object composed of a light reflected from the object is captured by the video camera 11a. Namely, the video camera 11a is an example of an imaging unit that captures an image of an object. Then, a video signal representing the image of the object is output from the video camera 11a to the signal cable 1b. This video signal is sent to the video processor 3 via the signal cable 1b. Based on this video signal, a moving image is generated by the video processor 3. This moving image is displayed on the monitor 4. If the video recorder 5 is set to a recording state by an operator, the above moving image is recorded by the video recorder 5.

(Drive of Laser Diode 2a)

When a set value is input by the input unit 2f, the pulse setting unit 2h sets the conditions of the pulse current for setting the amount of light of the laser diode 2a accumulated in a predetermined period to the set value input by the input unit 2f, based on the information stored in the storage unit 2g. Specifically, the input unit 2f changes at least one of the pulse width Tw, the number N of pulses, or the pulse amplitude Id according to a difference between a past set value and a new set value. For example, the pulse setting unit 2h changes only the pulse width Tw while keeping the number N of pulses and the pulse amplitude Id constant. In this case, the duty ratio is changed. Alternatively, the pulse setting unit 2h may change only the pulse amplitude Id while keeping the pulse width Tw and the number N of pulses constant. In this case, the duty ratio (a ratio of the pulse width TW and the pulse interval) is fixed. It is preferable that the duty ratio be 1:1 at a maximum, and that a pulse drive off time be larger than a pulse drive on time in order to suppress a temperature increase of the laser diode 2a. Then, the pulse setting unit 2h notifies the driver 2e of a newly set pulse width Tw, number N of pulses, and pulse amplitude Id as pulse conditions. If one or some of the pulse width Tw, the number N of pulses, and the pulse amplitude Id is/are to be kept constant, as described above, the pulse setting unit 2h may notify the driver 2e of only a value to be changed.

The bias setting unit 2k sets a magnitude of a bias current and notifies the driver 2e of the magnitude as a bias condition. The bias setting unit 2k determines the magnitude of the bias current within a range where the laser diode 2a does not emit a laser light only by the bias current. The bias setting unit 2k may set the magnitude of the bias current to zero. The setting of the magnitude of the bias current will be detailed later.

The driver 2e generates a drive current as a current obtained by superimposing a pulse current according to the pulse conditions notified from the pulse setting unit 2h on a bias current having the magnitude notified from the bias setting unit 2k. At this time, the driver 2e sets the pulse amplitude of the pulse current to a value obtained by subtracting the magnitude of the bias current from the pulse amplitude Id according to the pulse conditions. As a result, the driver 2e sets the pulse amplitude of the drive current to the pulse amplitude Id according to the pulse conditions. Then, the driver 2e applies the thus generated drive current to the laser diode 2a.

Since the laser diode 2a does emit the laser light only by the bias current, the laser diode 2a ordinarily repeats an emission state and a non-emission state in accordance with the pulse current irrespective of the magnitude of the bias current.

At this time, if the magnitude of the bias current is zero, the laser diode 2a changes in a very short time to a high-output laser mode after going through an LED emission mode and a laser oscillation mode. Thereafter, the laser diode changes in a very short time to a state in which no drive current is applied at all in an order opposite to that described above. Such state changes are repeated at a high frequency. As a result, local heat generation occurs in the laser diode 2a due to local current concentration. The heat generation may generate a defect or light-absorbing region in the laser diode, or may promote the propagation of such a defect or region.

On the other hand, if the magnitude of the bias current is an appropriate value that is not zero, the degree of the state change of the laser diode 2a is smaller than that described above, and deterioration of the laser diode 2a is suppressed. However, the bias current does not directly contribute to the emission of the laser light, and power consumption is increased as compared to a case where the magnitude of the bias current is zero.

(Determination of Operation Mode)

If the power supply circuit 6 is connected to an external power source and power is properly supplied from the external power source to the power supply circuit 6, the operating power of the various electrical elements of the endoscope system 100 is supplied from the power supply circuit 6. On the other hand, if the power supply circuit 6 is not connected to an external power source, or power is not properly supplied from an external power source to the power supply circuit 6, the operating power of the various electrical elements of the endoscope system 100 is supplied from the battery 7.

The endoscope system 100 is typically used while being kept in a treatment room in a medical facility. In this usage state, the endoscope system 100 is generally able to properly receive power supplied from an external power source. In such a usage state, the endoscope system 100 is often used continuously over a relatively long period of time. A treatment room is often fully equipped with air conditioning. Thus, the change in the ambient temperature is small, and the ambient temperature is maintained at, for example, about 25° C. Since similar examinations and treatments are often performed repeatedly, similar values are often set repeatedly as the set values of the amount of light of the laser diode 2a accumulated in a predetermined period, and a peak tends to occur in a frequency distribution of the set values.

On the other hand, the endoscope system 100 is operable by power supply from the battery 7 even in an environment where external power cannot be obtained. Such an operation state is assumed to be a case where the endoscope system 100 is moved to various places outside the treatment room and used therein, that is, a usage state in which an urgent examination that is not a normal examination, for example, is performed. In such a usage state, the continuous operating time of the endoscope system 100 is relatively short. Since the place where the endoscope system 100 is used changes, the ambient temperature may also change. In addition, since the content of the examination varies, the set value of the amount of light of the laser diode 2a accumulated in a predetermined period also varies depending on the content of the examination, likely causing the frequency distribution of the set values to vary.

Accordingly, the mode determining unit 2j monitors the operation state of the power supply circuit 6, and determines, as an operation mode, the first mode when power is properly supplied from the power supply circuit 6 because of external power being supplied, and determines the second mode as an operation mode in the other states.

When the operation mode is the first mode, the bias setting unit 2k sets, based on the information accumulated in the information accumulating unit 2i, the magnitude of the bias current to a value that is not zero within a range where the laser diode 2a does not emit a laser light only by the bias current. As an example, the bias setting unit 2k determines the magnitude of the bias current to a magnitude that can maintain the laser oscillation mode.

When the operation mode is the second mode, the bias setting unit 2k sets the magnitude of the bias current to zero.

FIG. 2 is a diagram showing a relationship between the supply state of the external power and the state of the drive current.

As shown in FIG. 2, the drive current includes the bias current when the power supply from the external power source is on, and does not include the bias current when the power supply from the external power source is off. The period of the first mode and the period of the second mode shown in FIG. 2 indicate the case where the set values of the amount of light of the laser diode 2a accumulated in a predetermined period are the same. In FIG. 2, the pulse amplitude is indicated as Ip, and the magnitude of the bias current is indicated as Ib.

Even if the power supply from the external power source is off, the mode determining unit 2j may set the operation mode to the first mode if the set value is equal to or greater than a predetermined value. Alternatively, if the power supply from the external power source is off, the pulse setting unit 2h may set only a set value that does not greatly deteriorate the laser diode 2a even when the operation mode is set to the second mode.

Advantageous Effects

As a result, when the power supply from the external power source is on and in an operation state where it is easy for the deterioration of the laser diode 2a to progress, the deterioration of the laser diode 2a can be suppressed by the application of the bias current, and high reliability can be maintained. When the power supply from the external power source is off and in an operation state where there is little concern about deterioration of the laser diode 2a, power saving can be achieved by not applying the bias current.

Second Embodiment

Figure 3:
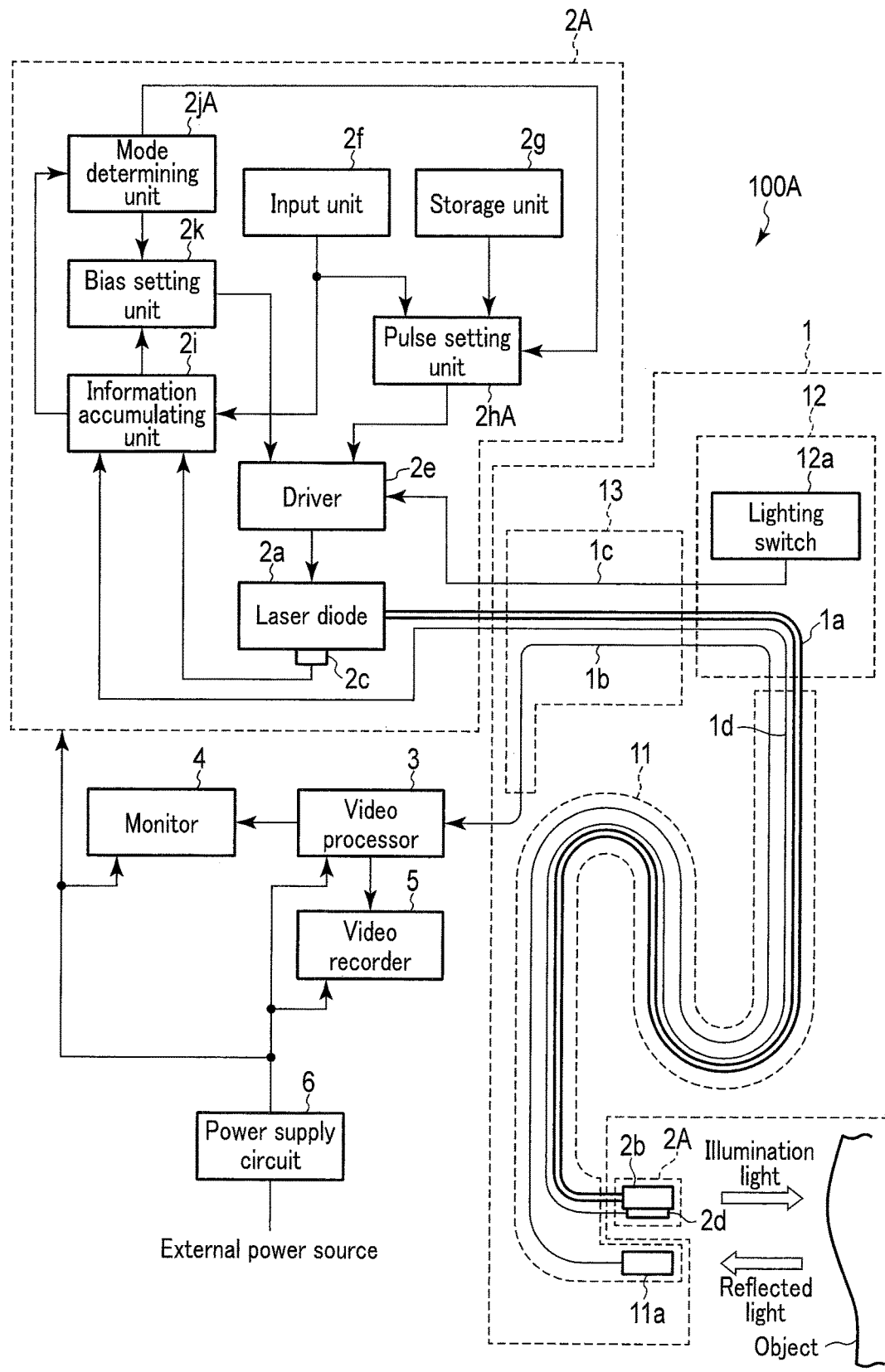
FIG. 3 is a block diagram showing a configuration of an endoscope system according to a second embodiment.

FIG. 3 is a block diagram showing a configuration of an endoscope system 100A according to a second embodiment. In FIG. 3, the same elements as those in FIG. 1 are denoted by the same reference symbols, and a detailed description thereof will be omitted.

The endoscope system 100A includes the endoscope 1, a light source device 2A, the video processor 3, the monitor 4, the video recorder 5, and the power supply circuit 6. Namely, the endoscope system 100A includes the light source device 2A instead of the light source device 2 of the endoscope system 100. The endoscope system 100A does not include the battery 7. However, the endoscope system 100A may include the battery 7 as the endoscope system 100 does.

The light source device 2A includes the laser diode 2a, the light converting member 2b, the temperature sensor 2c, the light amount sensor 2d, the driver 2e, the input unit 2f, the storage unit 2g, a pulse setting unit 2hA, the information accumulating unit 2i, a mode determining unit 2jA, and the bias setting unit 2k. Namely, the light source device 2A includes the pulse setting unit 2hA and the mode determining unit 2jA instead of the pulse setting unit 2h and the mode determining unit 2j of the light source device 2.

The pulse setting unit 2hA functions similarly to the pulse setting unit 2h. The pulse setting unit 2hA further functions to set pulse conditions for a test drive, which will be described later.

The mode determining unit 2jA determines an operation mode based on a change in an amount of an illumination light occurring when the laser diode 2a is test-driven by causing the pulse setting unit 2h to set the pulse conditions for the test drive.

Next, an operation of the endoscope system 100A configured as described above will be described. The operation of the endoscope system 100A differs from the operation of the endoscope system 100 in terms of the operation related to determination of an operation mode. Therefore, the operation related to determination of an operation mode will be exclusively described below.

(Determination of Operation Mode)

The mode determining unit 2jA starts a determination process at a predetermined determination timing. The mode determining unit 2jA may periodically start the determination process at regular intervals. The determination timing may be discretionary, and is set by, for example, a designer of the endoscope system 100A. Alternatively, the mode determining unit 2jA may set one of a plurality of candidate timings set by the designer, as the determination timing according to an instruction of a user.

In the present embodiment, the mode determining unit 2jA is implemented by a processor executing software processing. However, the mode determining unit 2jA may be implemented by other means such as a logic circuit.

Figure 4:
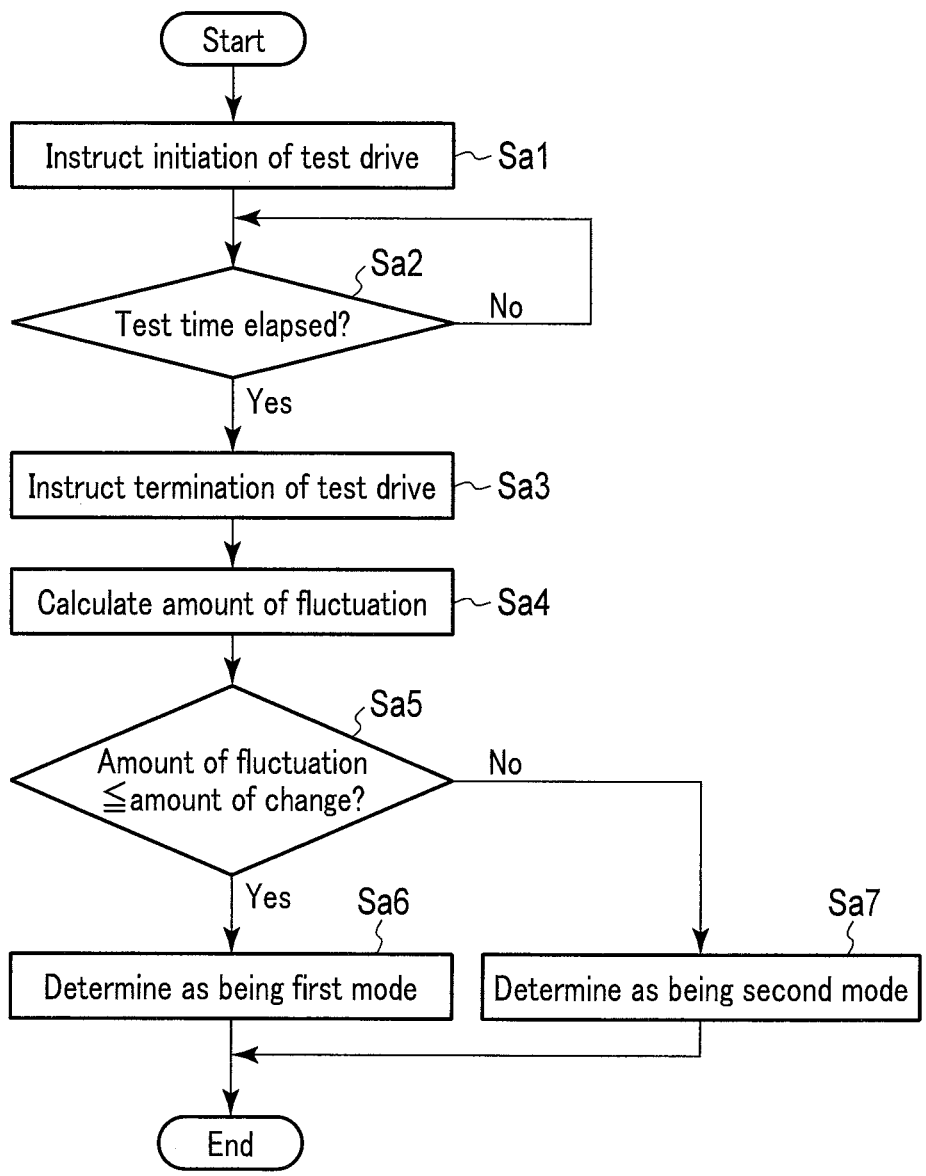
FIG. 4 is a flowchart of a determination process according to the second embodiment.

FIG. 4 is a flowchart of the determination process.

In step Sa1, the mode determining unit 2jA instructs the pulse setting unit 2hA to start a test drive.

Basically, the pulse setting unit 2hA operates similarly to the pulse setting unit 2h of the first embodiment. However, upon receiving the aforementioned instruction from the mode determining unit 2jA, the pulse setting unit 2hA determines pulse conditions for obtaining an accumulated light amount after a change made to an accumulated light amount corresponding to a set value as of the reception of the instruction by a predetermined amount of change, and notifies the pulse conditions to the driver 2e. The amount of change may be discretionary, and is, for example, set by a designer. As an example, it is assumed that the amount of change is set to "+5%." As a result, the driver 2e changes an amount of light emission of the laser diode 2a. This state is the test drive.

In step Sat, the mode determining unit 2jA waits for a predetermined test time to elapse after giving the instruction in step Sa1. The test time may be discretionary, and is, for example, set by a designer. However, the test time is set to be a time sufficient for the light amount detected by the light amount sensor 2d in the test drive state to be stored in the information accumulating unit 2i. When the test time has elapsed, the mode determining unit 2jA determines Yes in step Sat, and proceeds to step Sa3.

In step Sa3, the mode determining unit 2jA instructs the pulse setting unit 2h to stop the test drive. In response to this instruction, the pulse setting unit 2hA again notifies the driver 2e of the pulse conditions corresponding to the set value. As a result, the drive state of the laser diode 2a returns to the state before the initiation of the test drive.

In step Sa4, the mode determining unit 2j calculates an amount of fluctuation of the amount of the laser light due to the test drive. Specifically, the mode determining unit 2j reads the light amount detected by the light amount sensor 2d in a normal drive state before the initiation of the test drive and the light amount detected by the light amount sensor 2d in the test drive state from the information accumulating unit 2i, and calculates an amount of fluctuation as a difference between them.

In step Sa5, the mode determining unit 2j confirms whether or not the above calculated amount of fluctuation is equal to or less than the amount (predetermined amount) of change. If the amount of fluctuation is equal to or less than the amount of change, the mode determining unit 2j determines Yes and proceeds to step Sa6. If the amount of fluctuation is not equal to or less than the amount of change, the mode determining unit 2j determines No and proceeds to step Sa7.

In step Sa6, the mode determining unit 2j determines the operation mode to be the first mode.

In step Sa7, the mode determining unit 2j determines the operation mode to be the second mode.

When the mode determining unit 2j has finished determining an operation mode in step Sa6 or step Sa7, the mode determining unit 2j ends the determination process.

Advantageous Effects

When an actual amount of change of the laser light amount in the test drive is greater than an intended amount of change, it is considered that a relationship between a set light amount and the amount of the laser light becomes unstable due to heat generation of the laser diode 2a, etc. However, applying the second mode can suppress at least a fluctuation in the output of the laser diode 2a due to heat generation, and can reduce power consumption. On the other hand, if the amount of change of the laser light amount due to the test drive is equal to or less than an intended amount of change, an amount of an illumination light can be correctly adjusted by a prescribed change in the drive current. Namely, since a relationship between a set light amount and the amount of the laser light is stable, the first mode is applied.

Third Embodiment

FIG. 5 is a block diagram showing a configuration of an endoscope system 100B according to a third embodiment. In FIG. 5, the same elements as those in FIG. 1 are denoted by the same reference symbols, and a detailed description thereof will be omitted.

The endoscope system 100B includes the endoscope 1, a light source device 2B, the video processor 3, the monitor 4, the video recorder 5, and the power supply circuit 6.

Namely, the endoscope system 100B includes the light source device 2B instead of the light source device 2 of the endoscope system 100. The endoscope system 100B does not include the battery 7. However, the endoscope system 100B may include the battery 7 as the endoscope system 100 does.

The light source device 2B includes the laser diode 2a, the light converting member 2b, the temperature sensor 2c, the light amount sensor 2d, the driver 2e, the input unit 2f, the storage unit 2g, the pulse setting unit 2h, the information accumulating unit 2i, a mode determining unit 2jB, the bias setting unit 2k, and an operation timer 2m. Namely, the light source device 2B includes the mode determining unit 2jB instead of the mode determining unit 2j of the light source device 2, and includes an operation timer 2m.

The operation timer 2m is arranged at the distal end of the insertion module 11. Namely, the operation timer 2m is physically stored in the insertion module 11, but functionally belongs to the light source device 2B. The operation timer 2m measures a cumulative operating time of the laser diode 2a. The operation timer 2m can measure the cumulative operating time of the laser diode 2a by, for example, measuring a cumulative time of receiving an illumination light emitted from the light converting member 2b. In this case, a time during which a light amount detected by the light amount sensor 2d is equal to or greater than a threshold value may be counted. Alternatively, the operation timer 2m may be configured to measure a cumulative time of receiving a laser light emitted from the laser diode 2a. In this case, the measurement may be performed in the same manner as described above by using a laser light branched by a light branching section provided in the middle of the light guide 1a.

The mode determining unit 2jB determines an operation mode based on the operating time measured by the operation timer 2m.

Next, an operation of the endoscope system 100B configured as described above will be described. The operation of the endoscope system 100B differs from the operation of the endoscope system 100 in terms of the operation related to determination of an operation mode. Therefore, the operation related to determination of an operation mode will be exclusively described below.

(Determination of Operation Mode)

The operation timer 2m measures an operating time of the laser diode 2a as a cumulative time of a period during which a laser light emitted from the laser diode 2a can be detected. If the light source device 2B has a structure that allows replacement of the laser diode 2a, the operation timer 2m is reset when the laser diode 2a is replaced.

FIG. 6 is a diagram showing a relationship between the operating time and the state of the drive current.

The operating time gradually increases with the use of the laser diode 2a, as shown in FIG. 6. A change characteristic of the operating time is, in reality, not linear as shown in FIG. 6, but is shown in a linear shape in FIG. 6 for simplicity.

When the operating time measured by the operation timer 2m is less than a predetermined threshold time (predetermined time), the mode determining unit 2jB determines the second mode as an operation mode. When the operating time is equal to or longer than the threshold time, the mode determining unit 2jB switches the operation mode to the first mode.

The threshold time may be discretionary, and is, for example, set by a designer. However, it is preferable that the threshold time be appropriately set in consideration of the characteristics of the laser diode 2a. Specifically, the deterioration of the laser diode 2a gradually progresses with the operation. Also, an operation guarantee time may be set in the laser diode 2a by a manufacturer or the like, and the probability of deterioration is increased when the operation guarantee time passes. Therefore, it is assumed that the threshold time is set to be approximately the operation guarantee time, as an example. More specifically, it is assumed that the threshold time is longer than 100 hours.

Advantageous Effects

It is considered that in an unused state of the laser diode 2a there is hardly any factor in the laser diode 2a that causes or promotes deterioration of the laser diode 2a. Therefore, in this state, applying the second mode hardly promotes deterioration of the laser diode 2a. By adopting the second mode for the light source device 2B, power saving can be achieved.

However, repeatedly using the laser diode 2a increases a factor in the laser diode 2a that causes or promotes deterioration of the laser diode 2a. In such a state, applying the second mode may cause deterioration of the laser diode 2a to rapidly progress. However, adopting the first mode for the light source device 2B can suppress deterioration of the laser diode 2a and suppress reduction of the reliability.

Fourth Embodiment

FIG. 7 is a block diagram showing a configuration of an endoscope system 100C according to a fourth embodiment. In FIG. 7, the same elements as those in FIG. 1 are denoted by the same reference symbols, and a detailed description thereof will be omitted.

The endoscope system 100C includes the endoscope 1, a light source device 2C, the video processor 3, the monitor 4, the video recorder 5, and the power supply circuit 6. Namely, the endoscope system 100C includes the light source device 2C instead of the light source device 2 of the endoscope system 100. The endoscope system 100C does not include the battery 7. However, the endoscope system 100C may include the battery 7 as the endoscope system 100 does.

The light source device 2C includes the laser diode 2a, the light converting member 2b, the temperature sensor 2c, the light amount sensor 2d, the driver 2e, the input unit 2f, the storage unit 2g, the pulse setting unit 2h, the information accumulating unit 2i, a mode determining unit 2jC, and the bias setting unit 2k. Namely, the light source device 2C includes the mode determining unit 2jC instead of the mode determining unit 2j of the light source device 2.

The mode determining unit 2jC determines an operation mode based on a set value used by the pulse setting unit 2h.

Next, an operation of the endoscope system 100C configured as described above will be described. The operation of the endoscope system 100C differs from the operation of the endoscope system 100 in terms of the operation related to determination of an operation mode. Therefore, the operation related to determination of an operation mode will be exclusively described below.

(Determination of Operation Mode)

First, a threshold amplitude used for determining an operation mode will be described.

Figure 8:
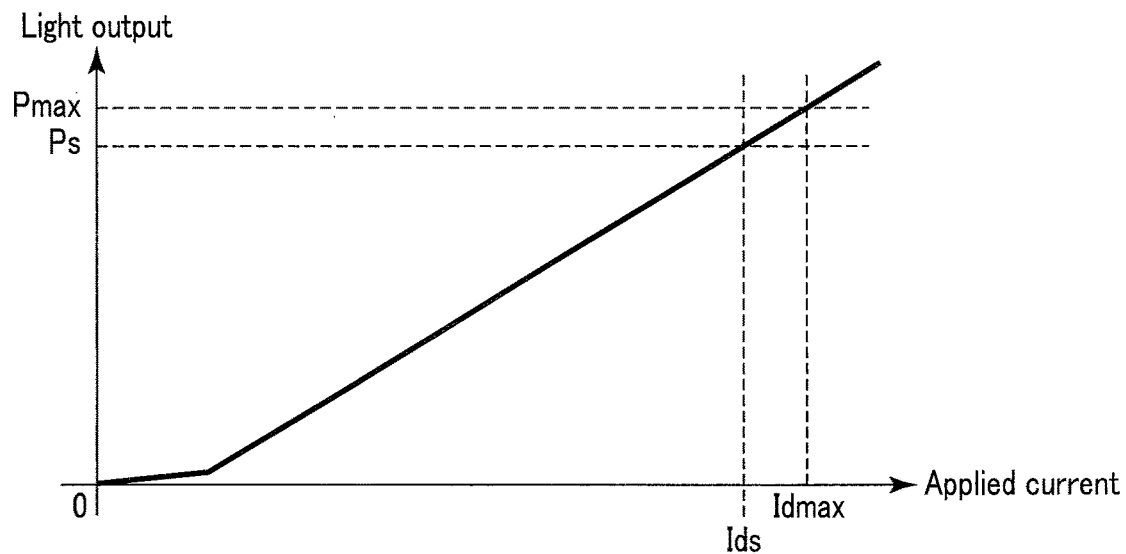
FIG. 8 is a diagram showing a relationship between an applied current and a light output of a laser diode, that is, the so-called I-L characteristics.

FIG. 8 is a diagram showing a relationship between the applied current and the light output of the laser diode 2a, that is, the so-called I-L characteristics.

From the operational circumstances of the endoscope system 100C, a maximum permissible value Pmax of the light output is, for example, set by a designer or the like. An applied current value for obtaining the maximum permissible value (maximum permissible light emission amount) Pmax as the light output is a maximum amplitude Idmax of the pulse current. A value obtained by multiplying the maximum permissible value Pmax by a coefficient of less than 1 is defined as a predetermined light emission amount Ps, and an applied current value for obtaining the predetermined light emission amount Ps as the light output is defined as a threshold amplitude Ids. The coefficient is, for example, 0.9. In this case, the predetermined light emission amount Ps is a value of 10% reduction of the maximum permissible value Pmax. However, the coefficient may be discretionarily set by a designer or the like. Also, the threshold amplitude Ids may be discretionarily set by a designer or the like as long as it is less than the maximum amplitude Idmax.

The mode determining unit 2jC performs a determination process for determining an operation mode. In the present embodiment, the mode determining unit 2jC is implemented by a processor performing the determination process as software processing. However, the mode determining unit 2jC may be implemented by other means such as a logic circuit.

Figure 9:
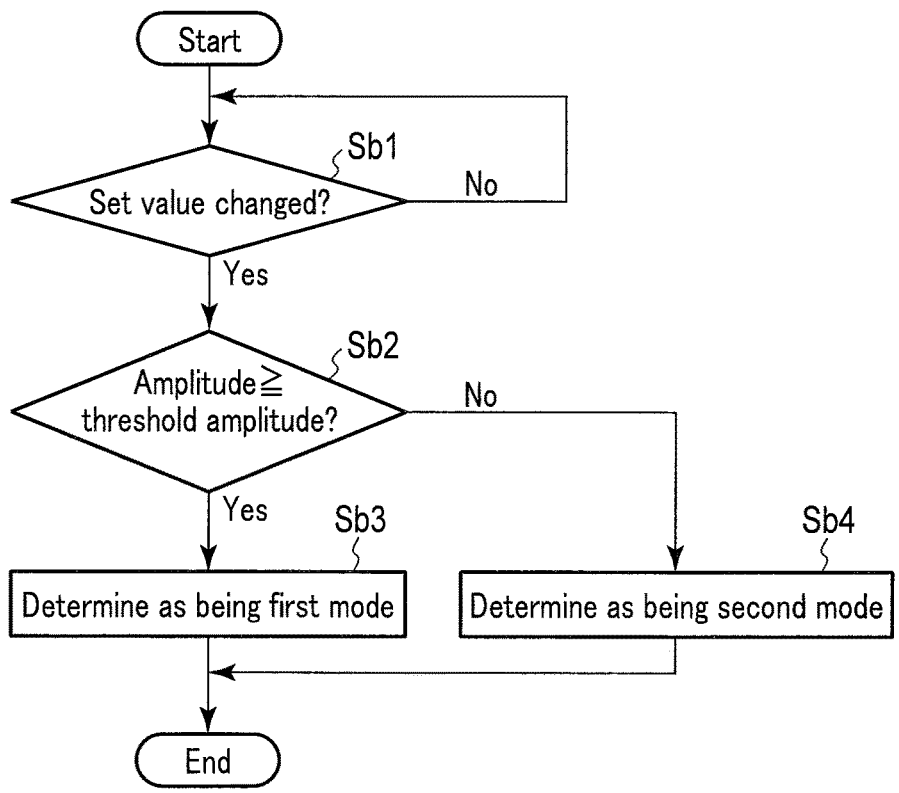
FIG. 9 is a flowchart of a determination process according to the fourth embodiment.

FIG. 9 is a flowchart of the determination process.

In step Sb1, the mode determining unit 2jC waits for a set value used by the pulse setting unit 2h to set the pulse conditions to be changed. When the set value is changed, the mode determining unit 2jC determines Yes and proceeds to step Sb2.

In step Sb2, the mode determining unit 2jC confirms whether or not the pulse amplitude Id set by the pulse setting unit 2h is equal to or greater than the threshold amplitude Ids. If the pulse amplitude Id is equal to or greater than the threshold amplitude Ids, the mode determining unit 2jC determines Yes and proceeds to step Sb3. If the pulse amplitude Id is less than the threshold amplitude Ids, the mode determining unit 2jC determines No and proceeds to step Sb4.

In step Sb3, the mode determining unit 2jC determines the operation mode to be the first mode.

In step Sb4, the mode determining unit 2jC determines the operation mode to be the second mode.

When the mode determining unit 2jC finishes determining the operation mode in step Sb3 or step Sb4, the mode determining unit 2jC ends the determination process.

In the present embodiment, if an accumulated light amount obtained by setting the duty ratio to a minimum value of 50% and setting the pulse amplitude Id to the maximum amplitude Idmax is equal to or less than the set value, the pulse setting unit 2h sets the pulse amplitude Id to the maximum amplitude Idmax. Then, the pulse setting unit 2h adjusts the duty ratio so that the obtained accumulated light amount becomes the set value. If the accumulated light amount obtained by setting the duty ratio to a minimum value of 50% and setting the pulse amplitude Id to the maximum amplitude Idmax is not equal to or less than the set value, the pulse setting unit 2h sets the duty ratio to the minimum value of 50%. Then, the pulse setting unit 2h adjusts the pulse amplitude Id so that the obtained accumulated light amount becomes the set value. Namely, the pulse setting unit 2h sets the pulse amplitude Id as large as possible at or below the maximum amplitude Idmax.

Advantageous Effects

As a result, when the pulse amplitude Id is less than the threshold amplitude Ids, the duty ratio is the minimum value, and the pulse amplitude Id is suppressed to be smaller than the maximum amplitude Idmax. Therefore, the amount of heat generated during a light emitting period of the laser diode 2a is small. Also, a non-emission period of the laser diode 2a is sufficiently long, and the heat generated during the light emitting period is sufficiently dissipated in the non-emission period. Therefore, in this state, applying the second mode hardly promotes deterioration of the laser diode 2a. By adopting the second mode for the light source device 2C, power saving can be achieved.

If the pulse amplitude is equal to or greater than the threshold amplitude Ids, the pulse amplitude is set to the maximum amplitude Idmax or a value close thereto. Therefore, the amount of heat generated during the light emitting period is large, and the heat may not be sufficiently dissipated during the non-emission period. Also, repeating a state where the drive current is zero, and a state of applying the drive current having a pulse amplitude near the maximum amplitude Idmax, may cause a delay in the response of the laser diode 2a to a rapid increase or decrease of an injection current. As a result, local concentration of current or generation of heat inside the laser diode 2a promotes generation, propagation, and migration of defects inside the laser diode 2a, and increases the risk of rapid progression of the deterioration of the laser diode 2a. However, adopting the first mode for the light source device 2C in such a situation can suppress deterioration of the laser diode 2a, and suppress a decrease in the reliability.

Fifth Embodiment

FIG. 10 is a block diagram showing a configuration of an endoscope system 100D according to a fifth embodiment. In FIG. 10, the same elements as those in FIG. 1 are denoted by the same reference symbols, and a detailed description thereof will be omitted.

The endoscope system 100D includes the endoscope 1, a light source device 2D, the video processor 3, the monitor 4, the video recorder 5, and the power supply circuit 6. Namely, the endoscope system 100D includes the light source device 2D instead of the light source device 2 of the endoscope system 100. The endoscope system 100D does not include the battery 7. However, the endoscope system 100D may include the battery 7 as the endoscope system 100 does.

The light source device 2D includes the laser diode 2a, the light converting member 2b, the temperature sensor 2c, the light amount sensor 2d, the driver 2e, the input unit 2f, the storage unit 2g, the pulse setting unit 2h, the information accumulating unit 2i, a mode determining unit 2jD, and the bias setting unit 2k. Namely, the light source device 2D includes the mode determining unit 2jD instead of the mode determining unit 2j of the light source device 2.

The mode determining unit 2jD determines an operation mode based on the pulse amplitude set by the pulse setting unit 2h.

Next, an operation of the endoscope system 100D configured as described above will be described. The operation of the endoscope system 100D differs from the operation of the endoscope system 100 in terms of the operation related to determination of an operation mode. Therefore, the operation related to determination of an operation mode will be exclusively described below.

(Determination of Operation Mode)

First, a current value to be focused on for determining an operation mode will be described.

Figure 11:
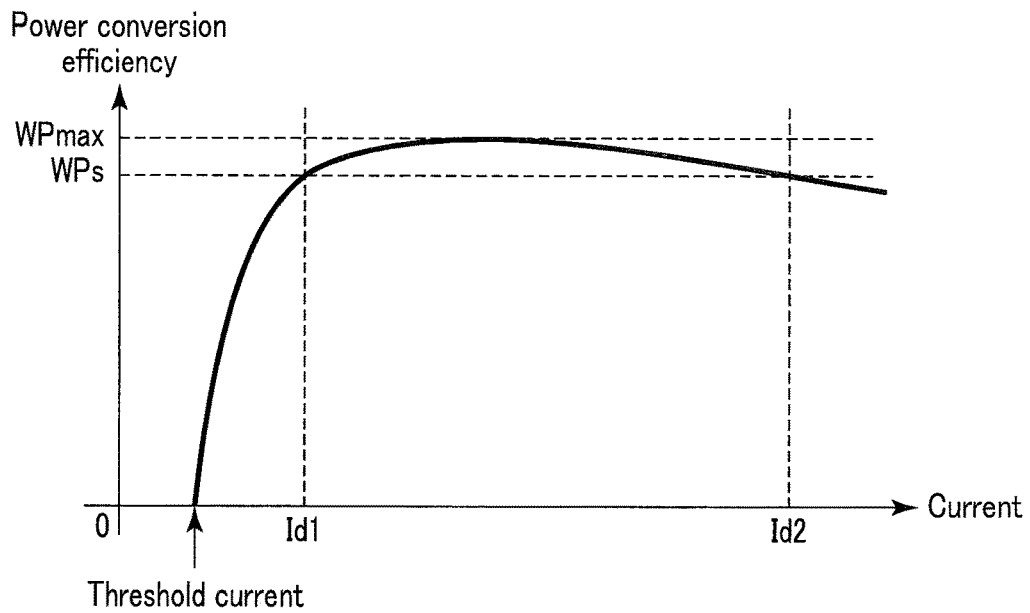
FIG. 11 is a diagram showing a relationship between an applied current and power conversion efficiency of a laser diode.

FIG. 11 is a diagram showing a relationship between the applied current and the power conversion efficiency of the laser diode 2a.

In the laser diode 2a, the power conversion efficiency becomes the maximum efficiency WPmax at a certain applied current, and when the applied current is increased or decreased therefrom, the power conversion efficiency decreases. A value obtained by multiplying the maximum efficiency WPmax by a coefficient of less than 1 is defined as a predetermined value WPs, and minimum and maximum applied current values, at which the predetermined value (predetermined efficiency value) WPs is obtained as the power conversion efficiency, are defined as Id1 and Id2. Namely, the applied current values Id1 and Id2 indicate the lower limit and the upper limit of a range (drive current range) of a value of the current to be applied to the laser diode 2a in order to obtain the power conversion efficiency of equal to or greater than the predetermined value WPs. The coefficient is, for example, 0.9. In this case, the value WPs is a value of a 10% reduction of the maximum efficiency WPmax. However, the coefficient may be discretionarily set by a designer or the like. Also, the value WPs may be discretionarily set by a designer or the like as long as it is less than the maximum efficiency WPmax.

The mode determining unit 2jD performs a determination process for determining an operation mode. In the present embodiment, the mode determining unit 2jD is implemented by a processor performing the determination process as software processing. However, the mode determining unit 2jD may be implemented by other means such as a logic circuit.

Figure 12:
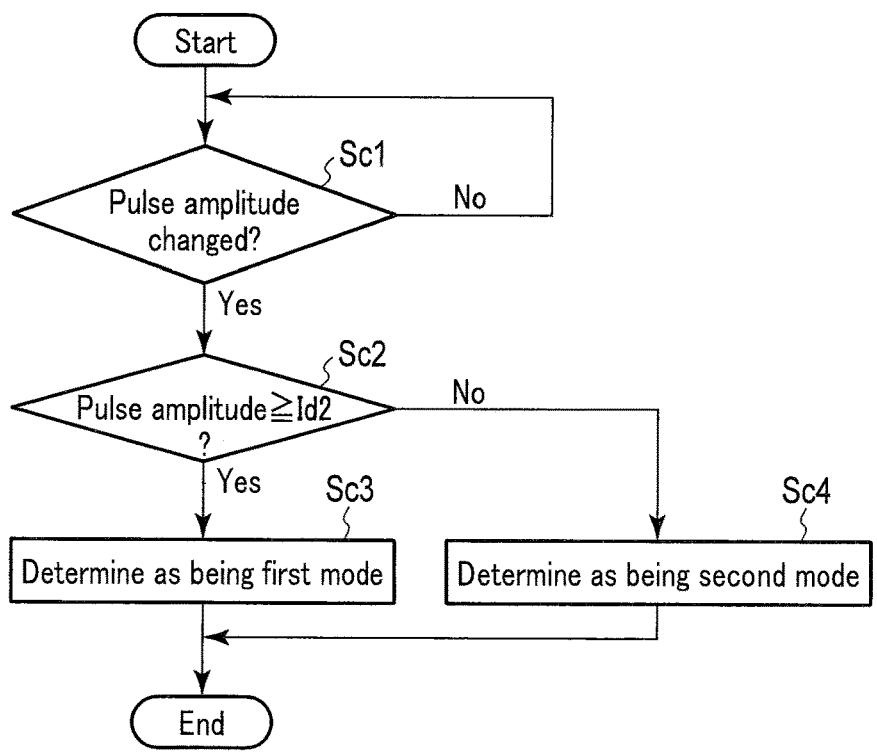
FIG. 12 is a flowchart of a determination process according to the fifth embodiment.

FIG. 12 is a flowchart of the determination process.

In step Sc1, the mode determining unit 2jD waits for the pulse amplitude to be changed by the pulse setting unit 2h. When the pulse amplitude is changed, the mode determining unit 2jD determines Yes and proceeds to step Sc2.

In step Sc2, the mode determining unit 2jD confirms whether or not the pulse amplitude Id set by the pulse setting unit 2h is equal to or greater than the amplitude Id2. If the pulse amplitude Id is equal to or greater than the amplitude Id2, the mode determining unit 2jD determines Yes and proceeds to step Sc3. If the pulse amplitude Id is less than the threshold amplitude Id2, the mode determining unit 2jD determines No and proceeds to step Sc4.

In step Sc3, the mode determining unit 2jD determines the operation mode to be the first mode.

In step Sc4, the mode determining unit 2jD determines the operation mode to be the second mode.

When the mode determining unit 2jD finishes determining an operation mode in step Sc3 or step Sc4, the mode determining unit 2jD ends the determination process.

As described above, when the pulse amplitude Id is in the range of Id1 to Id2, the laser diode 2a can efficiently emit a laser light. Therefore, in the present embodiment, the pulse setting unit 2h sets the pulse conditions to the extent possible so that the pulse amplitude Id is within the range of Id1 to Id2. However, the pulse setting unit 2h sets the pulse amplitude Id within the range of Id2 to the maximum amplitude Idmax when an accumulated light amount corresponding to a set value cannot be achieved by setting the pulse amplitude Id within the range of Id1 to Id2.

Advantageous Effects

As described above, when the pulse amplitude Id is set within the range of Id1 to Id2 by the pulse setting unit 2h, the operation mode is determined to be the second mode by the mode determining unit 2jD. When the pulse amplitude Id is set within the range of Id1 to Id2, the power conversion efficiency WP is held at a high level, and therefore the amount of heat generated by the laser diode 2a is nearly proportional to a total amount of the pulse current injected at a predetermined time. Accordingly, power saving can be achieved by applying the second mode.

On the other hand, when the pulse current is set so as to be greater than a value at which an amount of reduction of the power conversion efficiency is a predetermined percentage (10%), and to be not greater than the maximum amplitude Idmax, the operation mode is switched to the first mode. Since the power conversion efficiency WP decreases with respect to a set light amount, and the amount of the pulse current increases, the reliability degrades due to a rapid temperature rise, even if the heat generated in the laser diode 2a is sufficiently released from a housing surrounding the laser diode 2a. Therefore, setting a time to drive with a drive current applied with a bias to a time in which the laser diode 2a can hold the laser oscillation state, i.e., a period of at least 0.1 μs, and setting value of a bias current to a predetermined value, for example, a threshold current value of the laser diode 2a, before a rise and after falling of the pulse current, can ensure the reliability.

Sixth Embodiment

Figure 13:
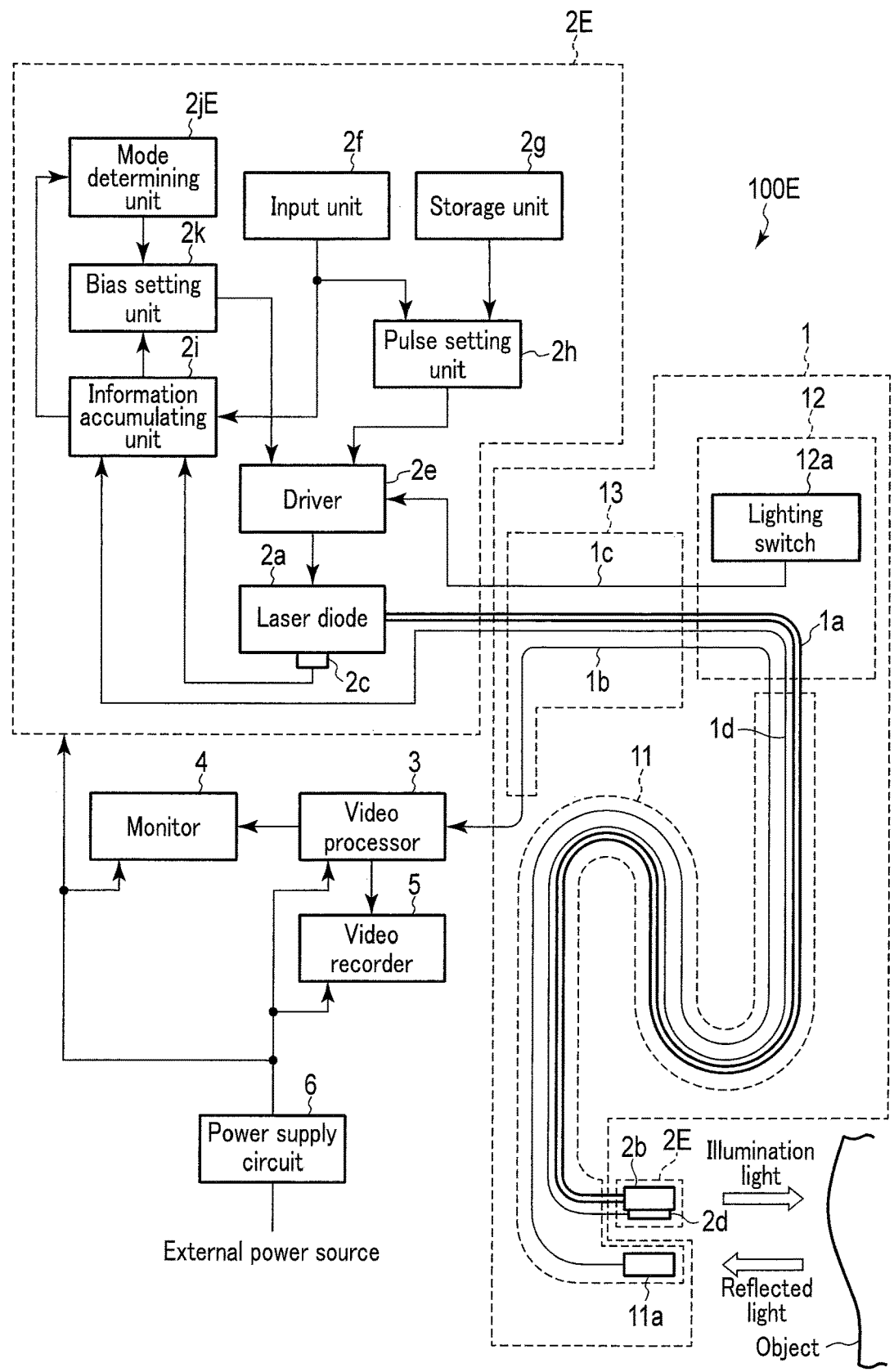
FIG. 13 is a block diagram showing a configuration of an endoscope system according to a sixth embodiment.

FIG. 13 is a block diagram showing a configuration of an endoscope system 100E according to a sixth embodiment. In FIG. 13, the same elements as those in FIG. 1 are denoted by the same reference symbols, and a detailed description thereof will be omitted.

The endoscope system 100E includes the endoscope 1, a light source device 2E, the video processor 3, the monitor 4, the video recorder 5, and the power supply circuit 6. Namely, the endoscope system 100E includes the light source device 2E instead of the light source device 2 of the endoscope system 100. The endoscope system 100E does not include the battery 7. However, the endoscope system 100E may include the battery 7 as the endoscope system 100 does.

The light source device 2E includes the laser diode 2a, the light converting member 2b, the temperature sensor 2c, the light amount sensor 2d, the driver 2e, the input unit 2f, the storage unit 2g, the pulse setting unit 2h, the information accumulating unit 2i, a mode determining unit 2jE, and the bias setting unit 2k. Namely, the light source device 2E includes the mode determining unit 2jE instead of the mode determining unit 2j of the light source device 2.

The mode determining unit 2jE determines an operation mode based on the frequency of the past set values accumulated in the information accumulating unit 2i.

Next, an operation of the endoscope system 100E configured as described above will be described. The operation of the endoscope system 100E differs from the operation of the endoscope system 100 in terms of the operation related to determination of an operation mode.

Therefore, the operation related to determination of an operation mode will be exclusively described below.

(Determination of Operation Mode)

Figure 14:
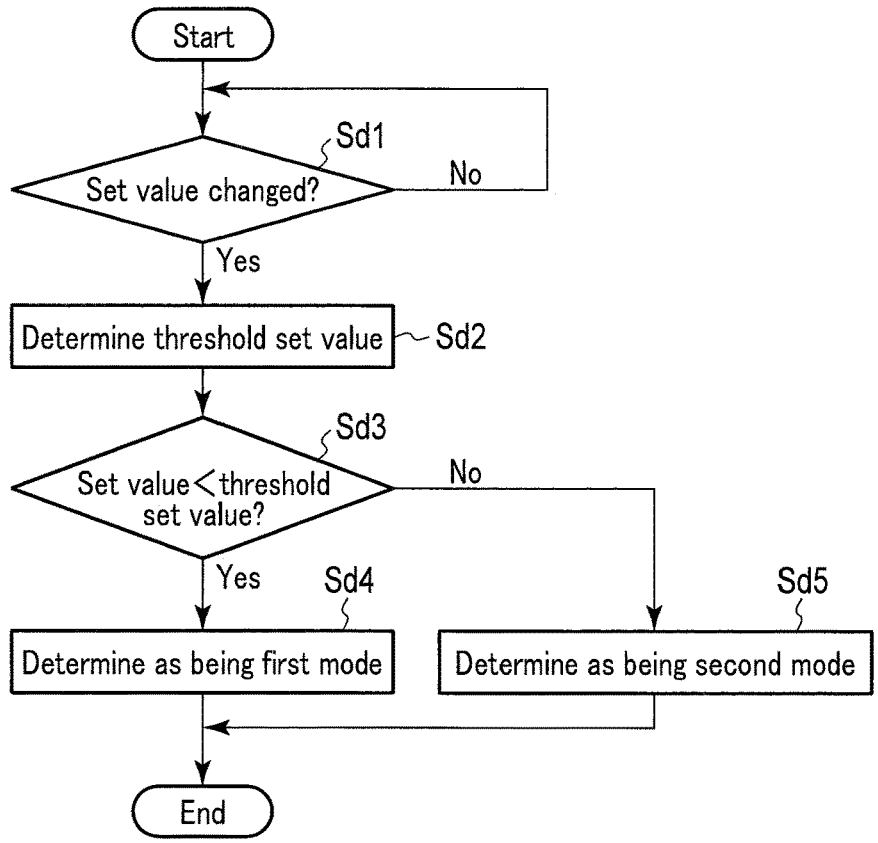
FIG. 14 is a flowchart of a determination process according to the sixth embodiment.

FIG. 14 is a flowchart of the determination process.

In step Sd1, the mode determining unit 2jE waits for a set value used by the pulse setting unit 2h to set the pulse conditions to be changed. When the set value is changed, the mode determining unit 2jE determines Yes and proceeds to step Sd2.

In step Sd2, the mode determining unit 2jE determines a threshold set value.

First, the mode determining unit 2jE obtains a frequency distribution of past set values based on the set values accumulated in the information accumulating unit 2i. Whether or not the mode determining unit 2jE considers the changed set value in order to obtain the frequency distribution of set values may be discretionary, and is, for example, determined by a designer or the like of the endoscope system 100E.

Figure 15:
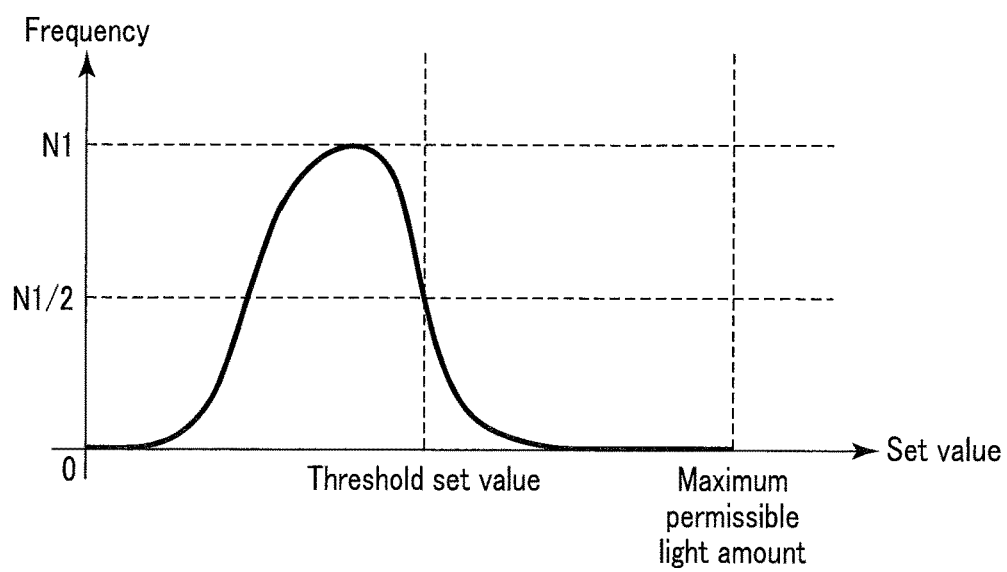
FIG. 15 is a diagram showing an example of a frequency distribution of set values.

FIG. 15 is a diagram showing an example of the frequency distribution of set values.

As shown in FIG. 15, the frequency distribution of set values often has the characteristics in which a frequency of a certain set value becomes the peak and the frequency decreases as the set value increases or decreases. The mode determining unit 2jE obtains a value N1/2, which is a half of a peak frequency value N1. When the frequency distribution of set values has the above characteristics, two set values usually appear as the set values at which the frequency becomes N1/2. The mode determining unit 2jE determines a larger one of the two set values as a threshold set value.

In step Sd3, the mode determining unit 2jE confirms whether or not the set value after being changed as described above is less than the threshold set value. If the set value is less than the threshold set value, the mode determining unit 2jE determines Yes and proceeds to step Sd4. If the set value is equal to or greater than the threshold set value, the mode determining unit 2jD determines No and proceeds to step Sd5.

In step Sd4, the mode determining unit 2jE determines the operation mode to be the first mode.

In step Sd5, the mode determining unit 2jE determines the operation mode to be the second mode.

When the mode determining unit 2jE finishes determining the operation mode in step Sd4 or step Sd5, the mode determining unit 2jE ends the determination process.

Advantageous Effects

As described above, the second mode is applied in regard to a set value having a high frequency of N1/2 or more, and a set value having a frequency lower than the frequency of N1/2 but corresponding to a low light amount, to thereby achieve power saving. In a general-use situation of the endoscope system 100E, a set value is determined by a doctor or a technician who sufficiently understands the characteristics of the endoscope system 100E. Such doctors or technicians often determine a set value within a range that allows stable operation of the endoscope system 100E, and the frequency of determining a set value large enough to require application of the first mode is low. Therefore, in a situation where a value set with a high frequency is set, the endoscope system 100E can be stably operated, and the second mode can be applied.

For a large set value that is determined at a low frequency, the first mode is applied to thereby ensure the reliability.

Accordingly, both high reliability and high efficiency can be achieved.

Seventh Embodiment

Figure 16:
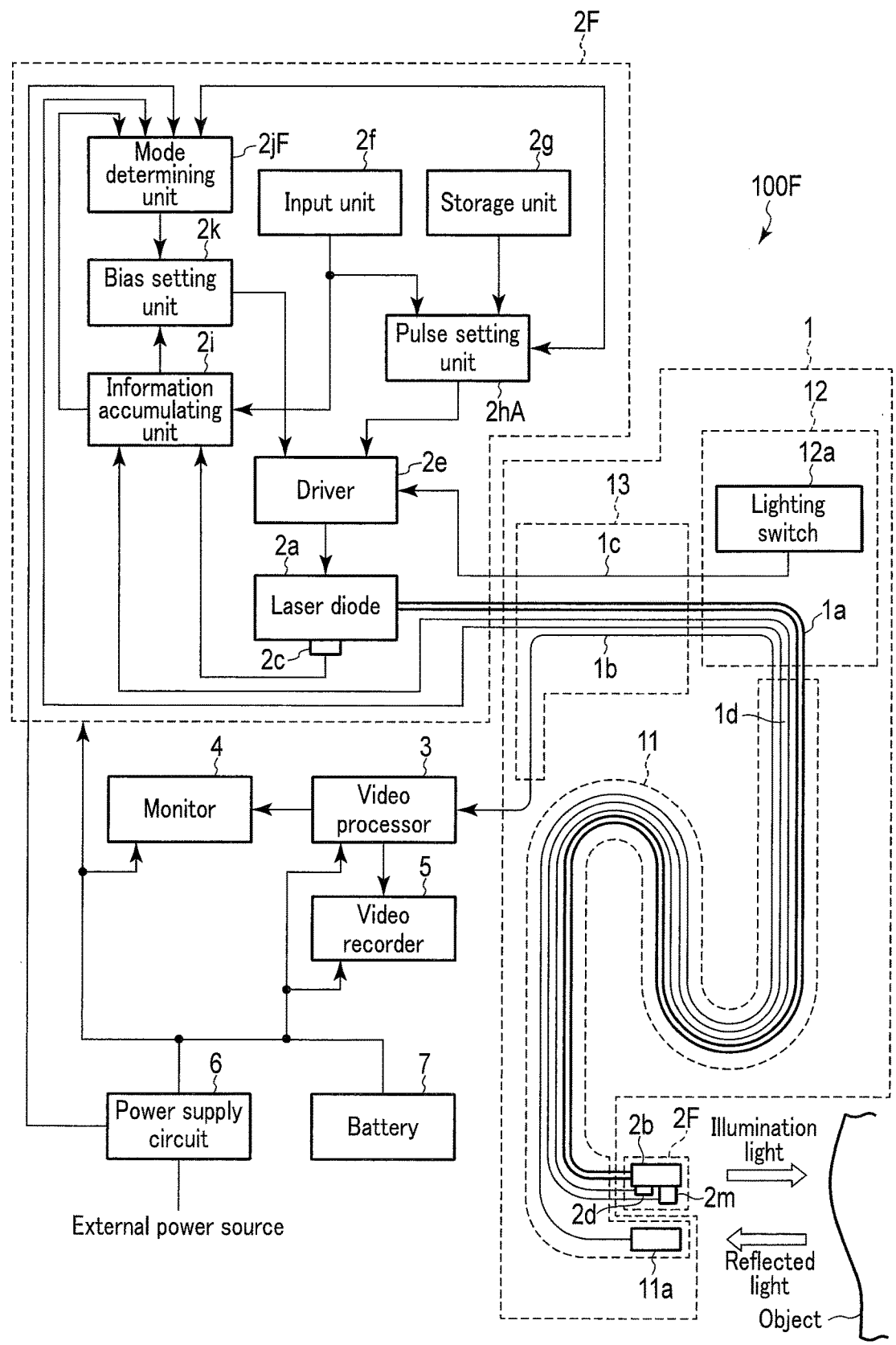
FIG. 16 is a block diagram showing a configuration of an endoscope system according to a seventh embodiment.

FIG. 16 is a block diagram showing a configuration of an endoscope system 100F according to a seventh embodiment. In FIG. 16, the same elements as those in FIG. 1, 3, or 5 are denoted by the same reference symbols, and a detailed description thereof will be omitted.

The endoscope system 100F includes the endoscope 1, a light source device 2F, the video processor 3, the monitor 4, the video recorder 5, the power supply circuit 6, and the battery 7. Namely, the endoscope system 100F includes the light source device 2F instead of the light source device 2 of the endoscope system 100.

The light source device 2F includes the laser diode 2a, the light converting member 2b, the temperature sensor 2c, the light amount sensor 2d, the driver 2e, the input unit 2f, the storage unit 2g, the pulse setting unit 2hA, the information accumulating unit 2i, a mode determining unit 2jF, the bias setting unit 2k, and the operation timer 2m. Namely, the light source device 2F includes the pulse setting unit 2hA and the mode determining unit 2jF instead of the pulse setting unit 2h and the mode determining unit 2j of the light source device 2, and includes the operation timer 2m.

The mode determining unit 2jF determines an operation mode based on at least two of (1) an operation state of the power supply circuit 6, (2) a change of an amount of an illumination light when the laser diode 2a is test-driven by causing the pulse setting unit 2h to set the pulse conditions for the test drive, (3) an operating time measured by the operation timer 2m, (4) a set value used by the pulse setting unit 2h, (5) a pulse amplitude set by the pulse setting unit 2h, or (6) a frequency of past set values accumulated in the information accumulating unit 2i.

Next, an operation of the endoscope system 100F configured as described above will be described. The operation of the endoscope system 100F differs from the operation of the endoscope system 100 in terms of the operation related to determination of an operation mode. Therefore, the operation related to determination of an operation mode will be exclusively described below.

(Determination of Operation Mode)

The mode determining unit 2jF executes at least two of the determination processes described in the first to sixth embodiments. As a result, the mode determining unit 2jF determines operation modes based on at least two of (1) to (6) above. The operation modes determined above are hereinafter referred to as preliminary determination modes. Namely, the mode determining unit 2jF determines a plurality of preliminary determination modes. The number of preliminary determination modes determined by the mode determining unit 2jF is indicated as Mmax in the description below.

In addition to the above, the mode determining unit 2jF performs a comprehensive determination process of determining an operation mode to be actually used by the bias setting unit 2k, based on the plurality of preliminary determination modes. The operation mode determined by the comprehensive determination process is referred to as a final determination mode.

Figure 17:
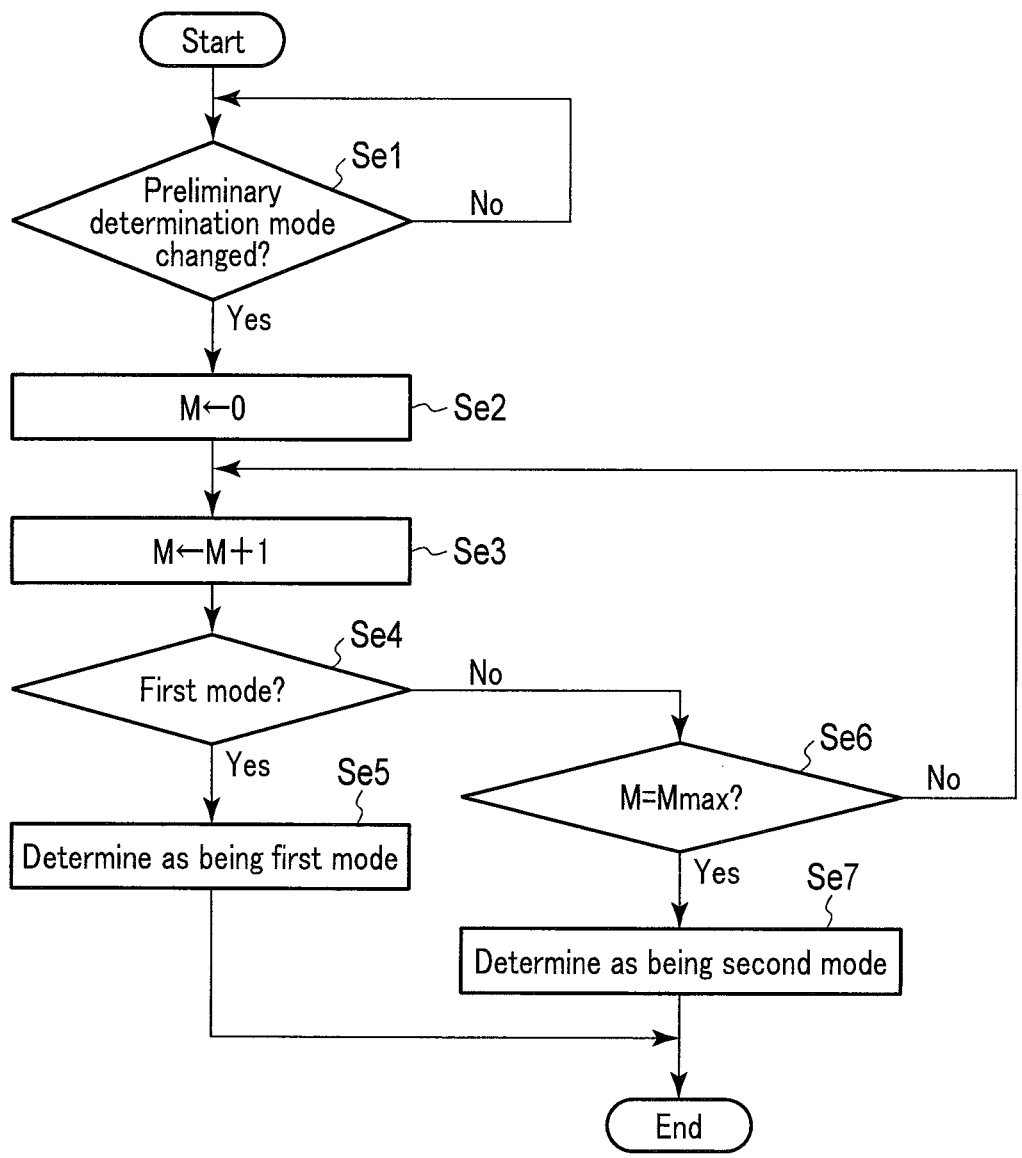
FIG. 17 is a flowchart of a comprehensive determination process.

FIG. 17 is a flowchart of the comprehensive determination process.

In step Se1, the mode determining unit 2jF waits for a change to occur in any of the preliminary determination modes. When a change occurs in any of the preliminary determination modes, the mode determining unit 2jF determines Yes and proceeds to step Se2.

In step Se2, the mode determining unit 2jF sets 0 as a value of a variable M.

In step Se3, the mode determining unit 2jF increases the value of the variable M by one.

In step Se4, the mode determining unit 2jF selects one of the preliminary determination modes that have not yet been selected, and confirms whether or not the first mode is determined as the preliminary determination mode. If the first mode is determined, the mode determining unit 2jF determines Yes and proceeds to step Se5.

In step Se5, the mode determining unit 2jF determines the first mode as the final determination mode. The mode determining unit 2jF then ends the comprehensive determination process.

On the other hand, if the second mode is determined as the selected preliminary determination mode in step Se4, the mode determining unit 2jF determines No and proceeds to step Se6.

In step Se6, the mode determining unit 2jF confirms whether or not the value of the variable M has reached Mmax. If the value of the variable M has not reached Mmax, the mode determining unit 2jF determines No and returns to step Se3. Namely, if the second mode is determined as the selected preliminary determination mode and there is an unselected preliminary determination mode, the mode determining unit 2jF repeats step Se3 and the subsequent steps, and confirms whether or not the first mode is determined as another preliminary determination mode. If the value of the variable M has reached Mmax, the mode determining unit 2jF determines Yes in step Se6 and proceeds to step Se7.

In step Se7, the mode determining unit 2jF determines the second mode as the final determination mode. The mode determining unit 2jF then ends the comprehensive determination process.

The mode determining unit 2jF repeatedly performs the comprehensive determination process.

Advantageous Effects

As described above, if one of the preliminary determination modes determined based on a plurality of conditions is determined to be the first mode, the mode determining unit 2jF determines the first mode as the final determination mode. If all of the plurality of preliminary determination modes are determined to be the second mode, the mode determining unit 2jF determines the second mode as the final determination mode.

Thereby, in a situation where it is possible to determine that the reliability needs to be ensured based on any one of a plurality of conditions, the laser diode 2a is driven in the first mode, ensuring high reliability. In a situation where it is not determined that the reliability needs to be ensured based on any of a plurality of conditions, the laser diode 2a is driven in the second mode, achieving power saving.

Modifications

In each of the above embodiments, the driver 2e continuously applies a bias current in the first mode. However, in each embodiment, the form of application of a drive current by the driver 2e in the first mode can be modified. First to third modifications related to the form of application of a drive current will be described below.

First Modification

FIG. 18 is a diagram showing a first modification of the application condition of a drive current in the first mode. In FIG. 18, only the application condition of a drive current with respect to the time direction is shown in a double size of that shown in FIG. 2.

In the first modification, the driver 2e applies a bias current during periods P1 and P2 when the first mode is determined as an operation mode. Period P1 is a part of the period in which a pulsed drive current is not applied, the part being immediately before the pulsed drive current rises. Period P2 is a part of the period immediately after the pulsed drive current falls.

Periods P1 and P2 are set in advance by a designer or the like as periods over which the laser diode 2a can at least hold the laser oscillation state. Specifically, a lifetime of a current (injected carrier) injected into the laser diode 2a is, for example, 10 to 20 nS. If the laser diode 2a is a high-output multi-beam type, it takes, for example, ten times or more of the lifetime described above for a current in a current injection region to become uniform due to the diffusion effect. Thus, in this case, it is necessary to apply a current over at least 0.1 ρS in order to uniformly inject a current into the current injection region. Also, in this case, each of periods P1 and P2 are set to 0.1 ρS or more. If a pulsed drive current for laser emission is applied to the laser diode 2a in a state where the current in the current injection region is uniform, local heat generation due to local current concentration can be suppressed. Therefore, there is little fear that a defect or light-absorbing region is generated in the laser diode due to such heat generation, or that a propagation of such a defect or region is promoted. Namely, high reliability as described in the first embodiment can be achieved. In addition, it is sufficient if the current in the current injection region is uniform at the time of rise and at the time of fall of the pulsed drive current for laser emission, and the application of a bias current not necessary for that purpose does not contribute much to improving the reliability.

Accordingly, temporarily applying a bias current in the first mode, as shown in FIG. 18, makes it possible to efficiently improve the reliability while suppressing the power increase in the second mode in the first modification, as compared to the first embodiment.

Second Modification

FIG. 19 is a diagram showing a second modification of the application condition of a drive current in the first mode. In FIG. 19, only the application condition of a drive current with respect to the time direction is shown in a double size of that shown in FIG. 2.

In the second modification, the driver 2e applies a bias current in period P1 when the first mode is determined as an operation mode. The application of the bias current performed in period P2 in the first modification is not performed in the second modification.

As a result, when stopping the light emission, the laser diode 2a changes, in a very short time, from a high-output laser mode to a state where no drive current is applied at all. Therefore, the reliability decreases, as compared to the first modification. However, the influence on the deterioration of the laser diode 2a is smaller when the pulsed drive current falls than when the pulsed drive current rises. Therefore, applying the bias current at the time of rise can sufficiently improve the reliability, as compared to the second mode. According to the second modification, since the period of applying the bias current is shorter than in the first modification, power saving can be better achieved, as compared to the first modification.

Third Modification

FIG. 20 is a diagram showing a third modification of the application condition of a drive current in the first mode. In FIG. 20, only the application condition of a drive current with respect to the time direction is shown in a double size of that shown in FIG. 2.

In the third modification, when the first mode is determined as an operation mode, the driver 2e gradually increases the drive current from the zero level to the pulse amplitude IP of the pulsed drive current in period P1. In period P2, the driver 2e gradually decreases the drive current from the pulse amplitude IP of the pulsed drive current to the zero level. As a result, the driver 2e makes a current applied to the laser diode 2a, as well as the pulsed drive current for laser emission shown by a dashed line in FIG. 20, have a trapezoidal pulse shape.

The same effects as those of the first modification can be achieved by the application condition of the drive current in the third modification.

As a further modification of the third modification, the driver 2e may change the drive current from the pulse amplitude IP to the zero level at once without gradually changing the drive current in period P2.

[Others Regarding Driving of the Laser Diode 2a (Common to the Respective Embodiments)]

(Setting of the Drive Current Conditions in Consideration of the Power Conversion Efficiency)

Figure 21:
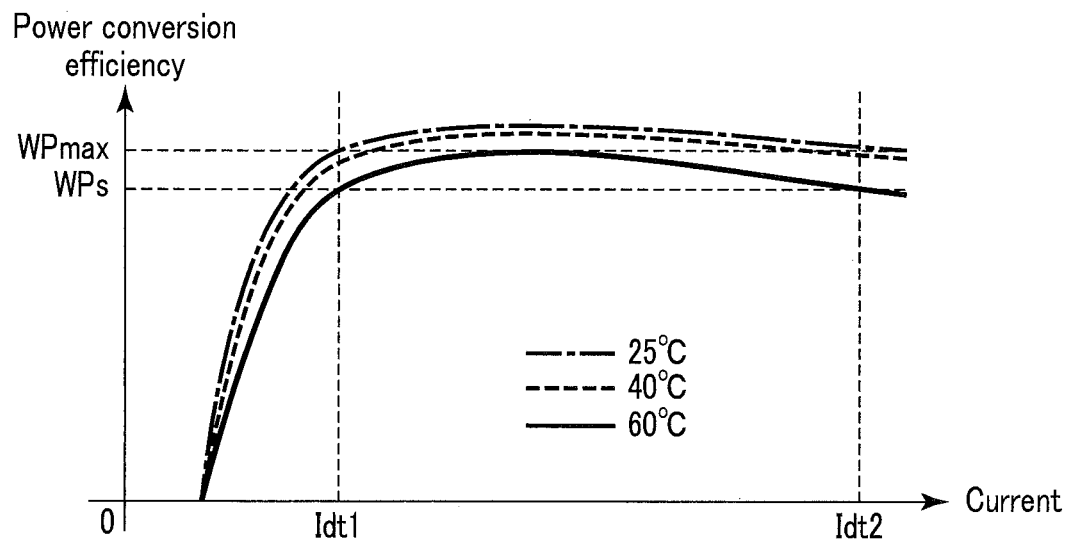
FIG. 21 is a diagram showing changes of power conversion efficiency with respect to an injection current in connection with a multimode high-output blue-light emitting laser diode.

FIG. 21 is a diagram showing changes, at ambient temperatures of 25° C., 40° C., and 60° C., respectively, of the power conversion efficiency with respect to the injected current for a multi-mode high-output blue-light emitting laser diode.

In the high-output blue-light emitting laser diode, the thermal conductivity of GaInN or AlGaN used as a material is approximately the same as or higher than that of glass, and is approximately four or more times larger than that of a GaAs- or InP-based material in the near-infrared region. Therefore, the resistance to deterioration of an emission end face of the laser diode, which influences the reliability of the laser diode, is very strong, and the decrease of the power conversion efficiency with respect to the rise of the ambient temperature is low.

In the case of using a high-output blue-light emitting laser diode as the laser diode 2a, applied current values Idt1 and Idt2 are set based on the characteristics of the ambient temperature in which the power conversion efficiency is relatively poor within an assumed ambient temperature range. For example, based on the characteristics of the case where the ambient temperature is 60° C., a value obtained by multiplying the maximum efficiency value WPmax of the power conversion efficiency by a coefficient of less than 1 is defined as a predetermined value WPs, and the minimum and maximum applied current values at which the predetermined value WPs or more is obtained as the power conversion efficiency are defined as Idt1 and Idt2. Namely, the applied current values Idt1 and Idt2 indicate the lower limit and the upper limit of a range of a value of the current to be applied to the laser diode 2a in order to obtain the power conversion efficiency of equal to or greater than the predetermined value WPs. The coefficient is, for example, 0.9. In this case, the predetermined value WPs is a value of a 10% reduction of the maximum efficiency WPmax. However, the coefficient may be discretionarily set by a designer or the like. Also, the predetermined value WPs may be discretionarily set by a designer or the like as long as it is less than the maximum efficiency WPmax.

When a set value is higher than a predetermined threshold set value, it is desirable to set the pulse amplitude for the drive current to Idts and set the duty ratio to be sufficiently large, thereby sufficiently releasing the heat generated at the time of light emission by the laser diode 2a when the light emission is stopped.

(Applied Pulse Width and Heat Generation of the Laser Diode 2a)

Figure 22:
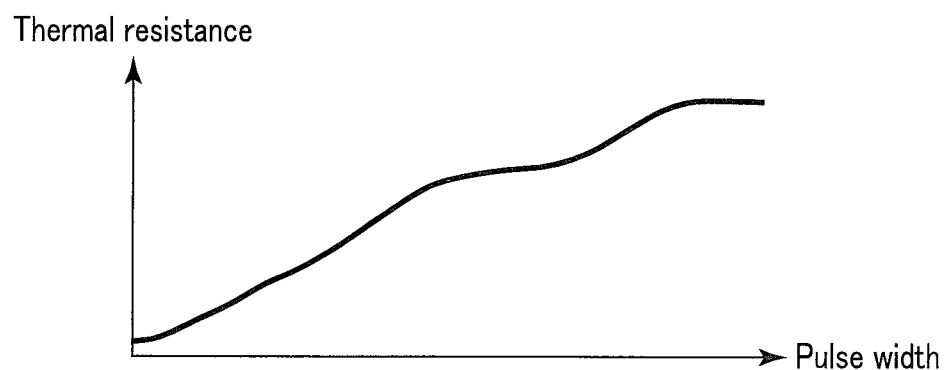
FIG. 22 is a diagram showing a relationship between a thermal resistance and a pulse width applied to a laser diode.

FIG. 22 is a diagram showing a relationship between a thermal resistance Rth and a pulse width Tw applied to the laser diode 2a. FIG. 22 shows an example of the case where a Can-type GaN laser diode is used as the laser diode 2a.

FIG. 22 specifically shows the result of measuring the thermal resistance Rth from the shift amount of the wavelength of the laser diode 2a due to the heat generated when the laser diode 2a is driven. The ambient temperature is set to 25° C., which is the standard state. FIG. 22 shows the change in the thermal resistance Rth when the laser diode 2a is driven while changing the applied pulse width Tw at the rated light output.

It is understood from FIG. 22 that as the applied pulse width Tw is shorter, the thermal resistance Rth becomes smaller, so that the temperature is less likely to rise. The thermal resistance Rth of a Can-type GaN high-output laser diode in the continuous wave (CW) state is an average value of about 15[° C./W]. On the other hand, the standard thermal resistance Rth of an AlGaAs laser diode with a wavelength of 810 nm in the near infrared range is about 50[° C./W]. This is because the thermal conductivity of a GaAs-based material covering the wavelength range of a red light or a near-infrared light is as small as ⅓ to ¼ of the thermal conductivity of glass, and the heat dissipation is not so good as compared to an InGaN-based material.

In order to reduce the thermal resistance Rth to at least ⅓ or less of the continuous wave (CW) state, it is preferable to set the pulse width to a pulse width Tw shorter than 10 ρS. In order to make heat generation inside the laser diode 2a almost negligible, it is preferable to set the pulse width Tw to equal to or less than 1 μs and implement high-speed pulse-drive.

In a further high-speed pulse operation of a nanosecond class, it is assumed that pulse driving is performed at a high frequency of about ¹⁄₁₀ of the relaxation frequency fm of about several GHz, which is unique to a semiconductor laser pulse operation, that is, a high frequency of about several 100 MHz. In this case, a time delay of laser oscillation or an overshoot phenomenon at the time of rising of the pulse occurs. This generates a sharp short pulse signal, and there is a risk that the peak pulse current will exceed the maximum permissible current of the laser diode 2a.

If the pulse width Tw exceeds the maximum permissible current even for a short period of nanoseconds, the laser diode 2a reduces the reflectance of the crystals of the reflecting mirrors provided on both end faces, causing a sudden deterioration of the laser diode 2a and rapidly degrading the reliability.

If the first mode in each of the above-described embodiments is applied, the laser diode 2a deals with the pulse current at a high speed, and no response delay occurs at the time of a rise or fall. Thus, the reliability is effectively improved.

The present embodiments can be modified in practice as described below.

The light source devices 2, 2A, 2B, 2C, 2D, 2E, and 2F may be implemented as independent devices without being incorporated in the endoscope systems 100, 100A, 100B, 100C, 100D, 100E, and 100F, or may be installed in any endoscope system to be used.

The endoscope 1 and the light source devices 2, 2A, 2B, 2C, 2D, 2E or 2F may be integrated with each other, and may be implemented as a wireless type which wirelessly transmits a video signal to the video processor 3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device comprising:
a laser diode configured to emit a laser light used as an illumination light;
a processor configured to determine one of a plurality of modes as an operation mode of the laser diode based on a usage state of the light source device; and
a driver configured to drive the laser diode in accordance with the operation mode determined by the processor,
wherein the determining of the one of the plurality of modes by the processor comprises:
selecting either a first mode in which the laser diode emits the laser light while the driver applies a bias current to the laser diode, or a second mode in which the laser diode emits the laser light while no bias current is applied to the laser diode by the driver,
selecting the second mode until a cumulative operating time of the laser diode as a usage state of the light source device reaches a threshold time set based on an operation guarantee time of the laser diode, and
selecting the first mode after the cumulative operating time reaches the threshold time;
wherein the driver is configured to apply, to the laser diode, the bias current having a magnitude that causes the laser diode to emit no laser light if the operation mode is the first mode.

2. The light source device according to claim 1, wherein stability of the laser diode varies depending on the mode selected from the plurality of modes, and
the processor is configured to select one of the plurality of modes based on a plurality of factors related to the usage state of the light source device, and is configured to determine the selected mode as the operation mode.

3. The light source device according to claim 2, wherein:
reliability of an operation of the laser diode in the second mode is lower than that in the first mode, and
power consumption of the laser diode in the second mode is smaller than that in the first mode,
the operation mode is configured to be selected from the first mode and the second mode, and
the processor is configured to select the first mode or the second mode based on each of the plurality of factors, and is configured to determine the first mode as the operation mode if the first mode is selected for at least one of the plurality of factors.

4. The light source device according to claim 1, wherein the driver is configured to supply a pulsed drive current to the laser diode, and is configured to apply the bias current to the laser diode during a period of time at least allowing the laser diode to maintain a laser oscillation state before initiation of application of the pulsed drive current if the operation mode is the first mode.

5. The light source device according to claim 4, wherein the driver is configured to apply the bias current to the laser diode during the period of time at least allowing the laser diode to maintain the laser oscillation state after completion of the application of the pulsed drive current.

* * * * *